United States Patent
Brophy

(10) Patent No.: US 7,709,200 B2
(45) Date of Patent: May 4, 2010

(54) ASSOCIATION OF PDE4D ALLELIC VARIANTS WITH STROKE

(75) Inventor: Victoria H. Brophy, Martinez, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 428 days.

(21) Appl. No.: 11/552,417

(22) Filed: Oct. 24, 2006

(65) Prior Publication Data

US 2007/0218472 A1    Sep. 20, 2007

Related U.S. Application Data

(60) Provisional application No. 60/730,248, filed on Oct. 25, 2005.

(51) Int. Cl.
*C07H 21/04* (2006.01)
*C12Q 1/68* (2006.01)

(52) U.S. Cl. .................. 435/6; 435/91.1; 435/91.2; 536/23.1; 536/24.3

(58) Field of Classification Search ............... None
See application file for complete search history.

(56) References Cited

U.S. PATENT DOCUMENTS

2003/0092019 A1*  5/2003  Meyer et al. ................. 435/6

FOREIGN PATENT DOCUMENTS

WO    WO 2004/028341 A2    8/2004

OTHER PUBLICATIONS

Gretarsdottir et al. (Nature Genetics, vol. 35, No. 2, pp. 131-138, Oct. 2003).*
Brophy et al. (Stroke, vol. 37, pp. 1385-1390, 2006).*
Zee et al. (Stroke, vol. 37, pp. 2012-2017, 2006).*
Rosand et al. (Nature Genetics, vol. 38, No. 10, Oct. 2006).*
Hirschhorn et al. (Genetics in Medicine. vol. 4, No. 2, pp. 45-61, Mar. 2002).*
Ioannidis (Nature Genetics, vol. 29, pp. 306-309, Nov. 2001).*
Brophy, V., et al., "Association of Phosphodiesterase 4D Polymorphisms With Ischemic Stroke in a US Population Stratified by Hypertension Status," *Stroke*, vol. 37(6), pp. 1385-1390 (Jun. 2006).
Worrall, B., et al., "PDE4D and Stroke: A Real Advance or a Case of the Emperor's New Clothes?" *Stroke*, vol. 37(8), pp. 1955-1957 (Aug. 2006).
Database DBSNP [Online] NCBI; SubSNP info for genotyping of RefSNP rs425384, "Submitted SNB (ss) Details: ss24715894," XP002414895, Database Accession No. ss24715894, abstract, 4 pgs. (Aug. 2004).
Database DBSNP [Online] NCBI; SubSNP info for genotyping RefSNP rs6450512, "Submitted SNP (ss) Details: ss24222464," XP002414896, Database Accession No. ss24222464, abstract, 4 pgs. (Aug. 2004).
Database Probe [Online] NCBI; Allele-specifi primers, "SSO probe for *H. sapiens* variation rs27171," XP002414897, Database Accession No. Pr044398, abstract, 1 pg. (May 2005).

* cited by examiner

*Primary Examiner*—Jeanine A Goldberg
(74) *Attorney, Agent, or Firm*—Townsend and Townsend and Crew LLP

(57) ABSTRACT

The present invention provides methods for detecting a predisposition for stroke in individuals by correlating allelic variants of the phosphodiesterase 4D (PDE4D) gene and hypertension status. The invention further contemplates kits and computer program products for detecting PDE4D polymorphisms indicative of a predisposition for stroke correlated with an individual's hypertension status.

15 Claims, 4 Drawing Sheets

ASSOCIATION OF PDE4D ALLELIC VARIANTS WITH STROKE

CROSS-REFERENCES TO RELATED APPLICATIONS

This application claims the benefit of U.S. Provisional Patent Application No. 60/730,248, filed on Oct. 25, 2005, the entire disclosure of which is hereby incorporated herein by reference in its entirety for all purposes.

BACKGROUND OF THE INVENTION

Recently the phosphodiesterase 4D (PDE4D) gene has been identified as a risk factor for ischemic stroke (Gretarsdottir, et al., *Am J Hum Genet* (2002) 70:593-603). Gretarsdottir et al. (2002) conducted a whole genome scan and found a linkage peak (LOD=4.4) on chromosome 5q121. Fine-mapping and association studies identified PDE4D as the gene linked to ischemic stroke in an Icelandic population (Gretarsdottir, et al., *Nat Genet* (2003) 35:131-138). Furthermore, mRNA levels of several PDE4D isoforms in transformed B-lymphocytes varied significantly between stroke cases and controls (Gretarsdottir, et al., (2003), supra).

PDE4D is a large gene that spans 1.5 Mb and has at least 22 exons and eight splice variants (Gretarsdottir, et al., (2003), supra; Wang, et al., *Cell Signal* (2003) 15:883-891; and Bolger, et al, *Biochem J* (1997) 328:539-548). PDE4D hydrolyzes cyclic AMP (cAMP) (Conti, et al., *J Biol Chem* (2003) 278:5493-5496) and is expressed in multiple tissues with varying expression patterns of the splice variants (Wang, et al., supra). PDE4D is found in brain, lung, kidney, macrophages, monocytes, B- and T-lymphocytes, and vascular smooth muscle cells (Bolger, et al., supra; Conti, et al., supra; and Pan, et al, *Biochem Pharmacol* (1994) 48:827-835). Several studies have reported PDE4D involvement in inflammation, proliferation, and migration, processes implicated in stroke occurrence (Ariga, et al., *J Immunol* (2004) 173:7531-7538; Miro, et al, *Biochem Biophys Res Commun* (2000) 274:415-421; Palmer, et al., *Circ Res* (1998) 82:852-861; Pan, et al, supra; and Johnson-Mills, et al., *Biochem Pharmacol* (1998) 56:1065-1073).

The association of specific PDE4D SNPs and haplotypes with stroke was initially identified in an Icelandic population (Gretarsdottir, et al., (2003), supra). However, until the present invention, the associations of specific PDE4D SNPs and microsatellites with stroke in specific subpopulations have not been evaluated. The present application addresses this need.

BRIEF SUMMARY OF THE INVENTION

The present invention is based on the discovery that the presence of at least one of an allele polymorphism of the phosphodiesterase 4D (PDE4D) gene is indicative of increased risk for suffering stroke in an individual based on their hypertension status, i.e., with or without hypertension. Polymorphisms predictive of the risk of stroke have been identified in individuals with or without hypertension.

Accordingly, in a first aspect, the invention provides for a method of predicting a predisposition for stroke in an individual without hypertension, the method comprising a) detecting in a sample from the individual the presence or absence of an allele comprising at least one polymorphism in the PDE4D locus, wherein the presence of the allele is associated with a predisposition for stroke in individuals without hypertension; and b) predicting the presence or absence of a predisposition for stroke in the person based on the presence or absence of the allele in the sample, wherein the presence of the allele is associated with a predisposition for stroke in individuals without hypertension. In one embodiment, the polymorphism is not predictive for stroke in individuals with hypertension. In one embodiment, the polymorphism is independently predictive for stroke in individuals with hypertension.

In another aspect, the invention provides for a method of predicting a predisposition for stroke in a person, the method comprising a) detecting in a sample from the person SNP 175 T/C of the PDE4D locus; and b) predicting the presence or absence of a predisposition for stroke in the person based on the presence or absence of an allele of the polymorphism in the sample, wherein the presence of T is associated with a predisposition for stroke in individuals with hypertension.

In a further aspect, the invention provides for a kit for predicting a predisposition for stroke in a person without hypertension, the kit comprising, a probe or primer that distinguishes between the A allele and the G allele of SNP 9 A/G; or a probe or primer that distinguishes between the C allele and the T allele of SNP 219 C/T; or a probe or primer that distinguishes between the C allele and the A allele of SNP 220 C/A.

Typically, the probe or primer distinguishes between polymorphism alleles in a polymerization dependent reaction, for example, polymerase chain reaction (PCR) or a primer extension reaction. The selective amplification of one allele of a polymorphism can be detected concurrently with an amplification reaction (i.e., "real-time") or subsequently to an amplification reaction.

In a further aspect, the invention provides for a kit for predicting a predisposition for stroke in a person with hypertension, the kit comprising, a probe or primer that distinguishes between the T allele and the C allele of SNP 175 T/C.

In a further aspect, the invention provides for a computer program product for use in predicting a predisposition for stroke in an individual, the computer program product comprising:

a computer readable medium encoded with program code, the program code comprising:

computer code for receiving, at a host computer, information indicating the presence of an allele of a polymorphism of the PDE4D locus associated with a predisposition for stroke in an individual, wherein the polymorphisms are selected from the group consisting of SNP 9 A/G, SNP 219 C/T, SNP 42 A/G, SNP 220 C/A, microsatellite repeats in AC008818-1 ($TCAT_8$, $TCAT_9$, $TCAT_{10}$, $TCAT_{11}$, $TCAT_{12}$ or $TCAT_{13}$), and SNP 175 T/C; and computer code for determining a predisposition for stroke in the individual, wherein a predisposition for stroke is predicted if the individual has:

an A in SNP 9 A/G;

a T in SNP 219 C/T;

a G in SNP 42 A/G;

a A in SNP 220 C/A;

9 microsatellite repeats (TCAT) within AC008818-1; or a T in SNP 175 T/C.

In a further aspect, the invention provides for a computer-implemented method for determining a predisposition for stroke in individuals, the method comprising:

receiving, at a host computer, information indicating the presence of an allele of a polymorphism of the PDE4D locus associated with a predisposition for stroke in an individual, wherein the polymorphisms are selected from the group consisting of SNP 9 A/G, SNP 219 C/T, SNP 42 A/G, SNP 220 C/A, microsatellite repeats (TCAT) in AC008818-1, and SNP 175 T/C; and determining a predisposition for stroke in the individual, wherein a predisposition for stroke is predicted if the individual has:
an A in SNP 9 A/G;
a T in SNP 219 C/T;
a G in SNP 42 A/G;
a A in SNP 220 C/A;
9 microsatellite repeats (TCAT) within AC008818-1; or
a T in SNP 175 T/C.

DETAILED DESCRIPTION OF THE INVENTION

1. Introduction

Figure 1A:
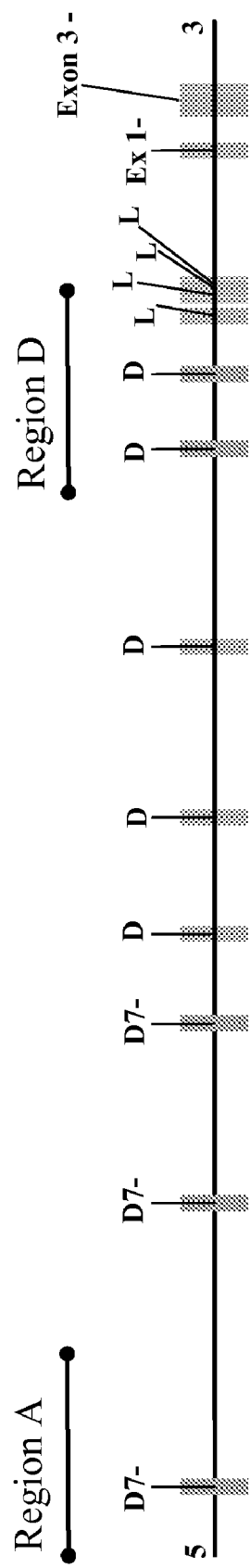
FIG. 1A) Structure of PDE4D. Each box represents an exon or series of exons and the two genotyped regions are shown by bars above the gene.
Figure 1B:
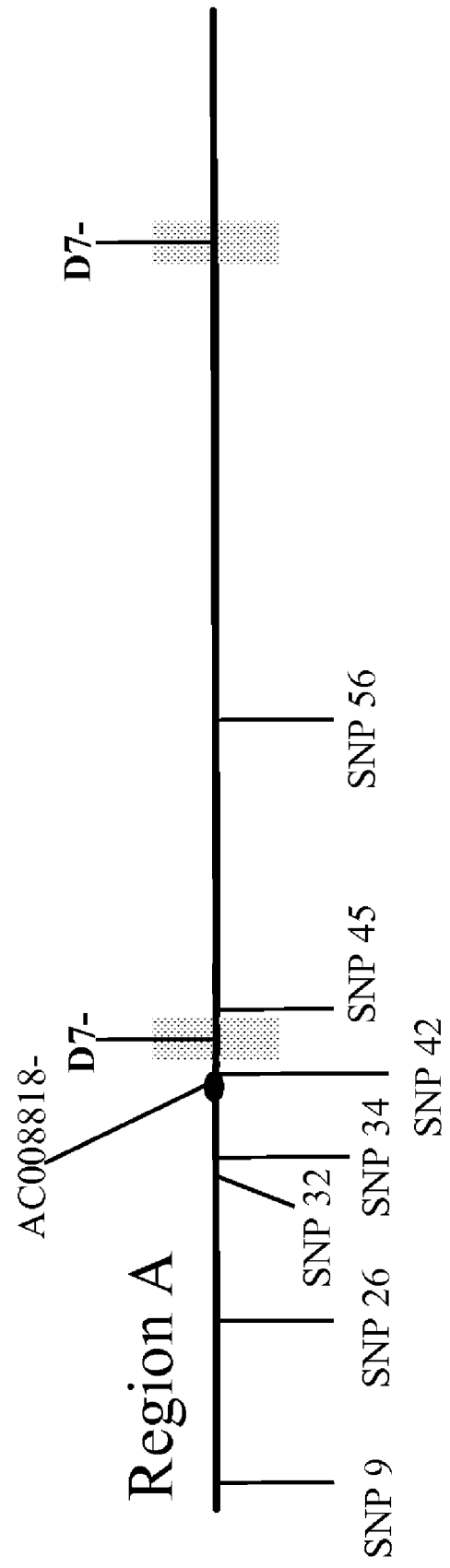
FIG. 1B) Polymorphisms genotyped in the A region FIG. 1C) Polymorphisms genotyped in the FIG. 1D region.
Figure 1C:
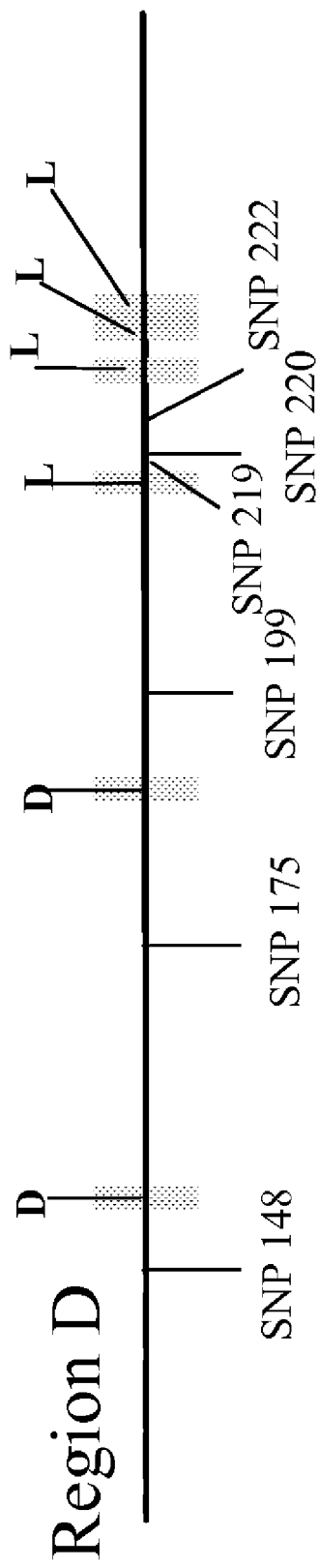
FIG. 1 illustrates a diagram of the PDE4D gene.

The present invention is based on the discovery of polymorphisms of the phosphodiesterase 4D (PDE4D) gene that are indicative of increased risk for stroke in an individual when correlated with an individual's hypertension status. While a number of genetic variants of PDE4D described herein have been previously identified, their presence or absence was not significantly correlated with predicted risk of stroke. However, the inventors have discovered that when stratifying individuals according to their hypertension status (i.e., with or without hypertension), certain polymorphisms, alone or combined, were identified whose presence or absence are predictive of risk for stroke.

2. Definitions

The term "stroke" refers to a cerebrovascular accident defined by an abrupt onset of a neurologic deficit attributable to a focal vascular disease (see, Chapter 349 of Kasper, et al., *Harrison's Principles of Internal Medicine*, 2005, 16th Edition, McGraw-Hill, hereby incorporated herein by reference). The term "stroke" includes any of the different clinically defined kinds of stroke, including without limitation, ischemic stroke, cardioembolic stoke, hemorrhagic stroke, atherothrombotic infarction, lacunar (small vessel) infarction, carotid stroke, large vessel stroke, etc.

The term "hypertension" as used herein refers to a condition in a subject having systolic blood pressure that is $\geq 160$ mmHg and/or diastolic blood pressure that is $\geq 90$ mmHg. Subjects having hypertension may also be taking thiazide diuretics. Hypertension is described in detail, for example, in Chapter 199 of *The Merck Manual of Diagnosis and Therapy*, 17th Edition, Beers and Berkow, eds., 2005, available on the worldwide web at merck.com/mrkshared/mmanual/home.jsp and in Chapter 230 of *Harrison's Internal Medicine*, 16th Edition, Kasper, et al, eds., 2005, the disclosures of both references are hereby incorporated herein by reference.

The term "predisposition" as used herein refers to an increased susceptibility to experiencing a stroke in a population or subpopulation of individuals. A predisposition can be measured in comparison to a general or unstratified population, a different subpopulation, or an identical subpopulation.

The phrase "associated with a predisposition for stroke" or "predictive of stroke" as used herein interchangeably refer to one or more polymorphisms (e.g. SNP, microsatellite, haplotype) or alleles, or combinations thereof, whose presence is statistically significantly correlated (i.e. a p-value less than 0.05) with an increased risk for the occurrence of stroke in a population of individuals. The association or correlation can be measured in comparison to a general or unstratified population, a different subpopulation, or an identical subpopulation. The population can be stratified or unstratified. The population can be defined by one or more parameters, for example, gender, race, ethnic origin, age, presence of another condition (e.g., presence of hypertension, absence of hypertension, obesity, diabetes, nicotine dependence).

The phrase "protective against stroke" refers to one or more polymorphisms statistically significantly correlated with a decreased incidence or lowered risk for occurrence of stroke in a population of individuals. The protective effect can be measured in comparison to a general or unstratified population, a different subpopulation, or an identical subpopulation. The population can be stratified or unstratified. The population can be defined by one or more parameters, for example, gender, race, ethnic origin, age, presence of another condition (e.g., presence of hypertension, absence of hypertension, obesity, diabetes, nicotine dependence).

The term "odds ratio" or "OR" refers to the ratio of the odds of having an event (e.g, a stroke) versus not having an event. If the OR is greater than one, the person has an increased risk of having an event, and if the OR is less than one, the person has a decreased risk of having an event. See, Norman and Streiner, *Biostatistics The Bare Essentials*, Second Edition, BC Decker Inc, 2000.

The term "hazard ratio" or "HR" refers to the probability of an event (e.g. stroke) at time t, given survival up to time t, and for a specific value of a prognostic variable (e.g. age, hypertension, etc). If the HR is greater than one, the person has an increased risk of having an event, and if the HR is less than one, the person has a decreased risk of having an event. See, Norman and Streiner, supra.

The term "relative risk" or "RR" refers to the ratio of the probability of having an event (e.g. stroke) in a first group as opposed to it occurring among those in a second group. Generally, the comparison is to an unselected general population of individuals. If RR is greater than one, the person has an increased risk of having an event, and if RR is less than one, the person has a decreased risk of having an event. See, Norman and Streiner, supra.

The terms "phosphodiesterase 4D" or "PDE4D" refer to a phosphodiesterase 4D protein that hydrolyzes cyclic AMP (cAMP), or a nucleic acid encoding the protein, including any splice variants, exons, introns, or untranslated regions. The term PDE4D usually refers to a genomic nucleic acid sequence. For example, PDE4D comprises at least about 80%, 85%, 90%, 95%, 96%, 97%, 98%, 99% sequence identity to SEQ ID NO:1 disclosed in U.S. Patent Publication No. 2005/0164220, or another genomic PDE4D nucleic acid sequence, including GenBank database accession numbers NT_086673, NT_006713 or AY406254. In other embodiments, PDE4D refers to an mRNA or a cDNA nucleic acid sequence, including any splice variants. For example, PDE4D can comprise at least about 80%, 85%, 90%, 95%, 96%, 97%, 98%, 99% sequence identity to GenBank database accession numbers NM_006203, BC036319, BC008390, AY245867, AY245866, AY388960, AF536977, AF536976, AF536975, U50159, U50158, U50157, U79571, AF012074, or AF012073.

In instances the polymorphism can result in a change in protein sequence. The change in protein sequence may affect protein function or not.

The PDE4D single nucleotide polymorphisms (SNPs) and microsatellite sequences referenced herein are numbered (i.e., SNP9) as previously described in U.S. Patent Publication 2005/0164220 and in Gretarsdottir, et al., *Nature Genetics* (2003) 35(2): 131-138, including all supplementary figures, tables, and sequence listings. Both of these references are hereby incorporated herein by reference in their entirety for all purposes. SNPs and microsatellite sequences discussed in the present application are described in Table 1, below.

TABLE 1

| SNP code | marker or exon | public name | start in NCBI build 33 (April 2003) | end in NCBI build 33 (April 2003) | start in SEQ ID NO: 1 of US Pat Pub. 2005/0164220 | end in SEQ ID NO: 1 of US Pat Pub. 2005/0164220 | within SEQ ID NO: in the present application |
|---|---|---|---|---|---|---|---|
| SNP 9 | SNP5PDM408531 | rs10074908 | 59805145 | 59805145 | 91470 | 91470 | SEQ ID NO: 1 |
| SNP 26 | SNP5PDM379372 | rs40512 | 59775992 | 59775992 | 120628 | 120628 | SEQ ID NO: 2 |
| SNP 32 | SNP5PDM370640 | rs456009 | 59767259 | 59767259 | 129361 | 129361 | SEQ ID NO: 3 |
| SNP 34 | SNP5PDM368135 | rs27653 | 59764755 | 59764755 | 131865 | 131865 | SEQ ID NO: 4 |
| SNP 42 | SNP5PDM361194 | rs153031 | 59757816 | 59757816 | 138806 | 138806 | SEQ ID NO: 5 |
| SNP 45 | SNP5PDM357221 | | 59753842 | 59753842 | 142780 | 142780 | SEQ ID NO: 6 |
| SNP 56 | SNP5PDM310653 | rs702553 | 59707298 | 59707298 | | | SEQ ID NO: 7 |
| SNP 148 | | rs154025 | 58639612 | 58639612 | | | SEQ ID NO: 13 |
| SNP 175 | SNP5PDM807403 | rs27171 | 58589414 | 58589414 | 1307403 | 1307403 | SEQ ID NO: 12 |
| SNP 199 | | rs27547 | 58525429 | 58525429 | | | SEQ ID NO: 11 |
| SNP 219 | SNP5PDM914804 | rs6450512 | 58482026 | 58482026 | 1414804 | 1414804 | SEQ ID NO: 10 |
| SNP 220 | SNP5PDM915979 | rs425384 | 58480851 | 58480851 | 1415979 | 1415979 | SEQ ID NO: 9 |
| SNP 222 | | | 58470907 | 58470907 | | | SEQ ID NO: 8 |
| microsatellite repeats in AC008818-1 | | | 59759882 | 59760075 | 136740 | 136547 | SEQ ID NO: 14 through SEQ ID NO: 19 |

The term "allele" refers to a nucleotide sequence variant of a gene of interest.

The term "genotype" refers to a description of the alleles of a gene contained in an individual or a sample. In the context of this invention, no distinction is made between the genotype of an individual and the genotype of a sample originating from the individual. Although typically a genotype is determined from samples of diploid cells, a genotype can be determined from a sample of haploid cells, such as a sperm cell.

A "polymorphism" refers to the occurrence of two or more genetically determined alternative sequences of a gene in a population. Typically, the first identified allelic form is arbitrarily designated as the reference form and other allelic forms are designated as alternative or variant alleles. The allelic form occurring most frequently in a selected population is sometimes referred to as the wildtype form.

The term "haplotype" refers to a combination of two or more alleles or two or more polymorphisms.

The term "linkage disequilibrium" as used herein, refers to alleles at different loci that are not associated at random, i.e., not associated in proportion to their frequencies. If the alleles are in positive linkage disequilibrium, then the alleles occur together more often than expected, assuming statistical independence. Conversely, if the alleles are in negative linkage disequilibrium, then the alleles occur together less often than expected assuming statistical independence.

A "single nucleotide polymorphism" or "SNP" is a site of one nucleotide that varies between alleles. Single nucleotide polymorphisms may occur at any region of the gene. In some A "microsatellite" refers to a class of DNA polymorphisms arising from a short base-pair sequence that is tandemly repeated a variable number of times. The short base pair sequence is usually about 1, 2, 3, 4, 5 or 6 nucleotide bases in length. A microsatellite can comprise, for example, about 5-100 or more tandem repeats, more usually about 5-50 or 5-25 tandem repeats, and typically about 5-15 or 5, 6, 7, 8, 9, 10, 11, 12, 13, 14 or 15 tandem repeats.

The term "hybridization" refers to the formation of a duplex structure by two single stranded nucleic acids due to complementary base pairing. Hybridization can occur between exactly complementary nucleic acid strands or between nucleic acid strands that contain minor regions of mismatch.

As used herein, the term "substantially complementary" refers to sequences that are complementary except for minor regions of mismatch. Typically, the total number of mismatched nucleotides over a hybridizing region is not more than 3 nucleotides for sequences about 15 nucleotides in length. Conditions under which only exactly complementary nucleic acid strands will hybridize are referred to as "stringent" or "sequence-specific" hybridization conditions. Stable duplexes of substantially complementary nucleic acids can be achieved under less stringent hybridization conditions. Those skilled in the art of nucleic acid technology can determine duplex stability empirically considering a number of variables including, for example, the length and base pair concentration of the oligonucleotides, ionic strength, and incidence of mismatched base pairs. Computer software for calculating duplex stability is commercially available from National Biosciences, Inc. (Plymouth, Minn.); the OLIGO version 5 reference manual is incorporated herein by reference.

Stringent, sequence-specific hybridization conditions, under which an oligonucleotide will hybridize only to the exactly complementary target sequence, are well known in the art (see, e.g. the general references provided in the section on detecting polymorphisms in nucleic acid sequences). Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the base pairs have dissociated. Relaxing the stringency of the hybridizing conditions will allow sequence mismatches to be tolerated; the degree of mismatch tolerated can be controlled by suitable adjustment of the hybridization conditions.

The term "primer" refers to an oligonucleotide that acts as a point of initiation of DNA synthesis under conditions in which synthesis of a primer extension product complementary to a nucleic acid strand is induced, i.e., in the presence of four different nucleoside triphosphates and an agent for polymerization (i.e., DNA polymerase or reverse transcriptase) in an appropriate buffer and at a suitable temperature. A primer is usually a single-stranded oligodeoxyribonucleotide. The primer includes a "hybridizing region" exactly or substantially complementary to the target sequence, usually about 15 to about 35 nucleotides in length. The use of modified bases or base analogues which affect the hybridization stability, which are well known in the art, may enable the use of shorter or longer primers with comparable stability. A primer oligonucleotide can either consist entirely of the hybridizing region or can contain additional features which allow for the detection, immobilization, or manipulation of the amplified product, but which do not alter the ability of the primer to serve as a starting reagent for DNA synthesis. For example, a nucleic acid sequence tail can be included at the 5'-end of the primer that hybridizes to a capture oligonucleotide.

An "allele-specific" primer, as used herein, is a primer that hybridizes to the target sequence such that the 3'-end, usually the 3'-terminal nucleotide, of the primer aligns with the polymorphic site of interest and is exactly complementary to one of the alleles at the polymorphic position. As used herein, the primer is "specific for" the allele to which it is exactly complementary at the 3'-end. In general, primer extension is inhibited when a mismatch is present at the 3'-end of the primer. An allele-specific primer, when hybridized to the exactly complementary allele, is extendable at a greater efficiency. The same primer, when hybridized to the other allele, is not readily extendable because of the mismatch at the 3'-end of the primer in the hybridization duplex. Thus, the use of an allele-specific primer provides allelic discrimination based on whether an appreciable extension product is formed. An allele-specific primer distinguishes one allele from another allele or other alleles.

The term "probe" refers to an oligonucleotide that selectively hybridizes to a target nucleic acid under suitable conditions. The probe hybridizing region is usually from about 10 to about 35 nucleotides in length, more usually from about 15 to about 35 nucleotides in length. The use of modified bases or base analogues which affect the hybridization stability, which are well known in the art, may enable the use of shorter or longer probes with comparable stability. A probe oligonucleotide can either consist entirely of the hybridizing region or can contain additional features which allow for the detection or immobilization of the probe, but which do not significantly alter the hybridization characteristics of the hybridizing region.

An "allele-specific" probe contains a "hybridizing region" exactly or substantially complementary to the target sequence, and is exactly complementary to the target sequence at the polymorphic site of interest. A hybridization assay carried out using the probe under sufficiently stringent hybridization conditions enables the selective detection of a specific target sequence. An allele-specific probe distinguishes one allele from another allele or other alleles.

The term "target sequence" or "target region" refers to a region of a nucleic acid that is to be analyzed and comprises the polymorphic site of interest.

As used herein, the terms "nucleic acid," "polynucleotide" and "oligonucleotide" refer to primers, probes, and oligomer fragments. The terms are not limited by length and are generic to linear polymers of polydeoxyribonucleotides (containing 2-deoxy-D-ribose), polyribonucleotides (containing D-ribose), and any other N-glycoside of a purine or pyrimidine base, or modified purine or pyrimidine bases. These terms include double- and single-stranded DNA, as well as double- and single-stranded RNA. Oligonucleotides of the invention may be used as primers and/or probes. Thus oligonucleotides referred to herein as "primers" may act as probes and oligonucleotides referred to as "probes" may act as primer in some embodiments.

A nucleic acid, polynucleotide or oligonucleotide can comprise phosphodiester linkages or modified linkages including, but not limited to phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, polynucleotide or oligonucleotide can comprise the five biologically occurring bases (adenine, guanine, thymine, cytosine and uracil) and/or bases other than the five biologically occurring bases. These bases may serve a number of purposes, e.g., to stabilize or destabilize hybridization; to promote or inhibit probe degradation; or as attachment points for detectable moieties or quencher moieties. For example, a polynucleotide of the invention can contain one or more modified, non-standard, or derivatized base moieties, including, but not limited to, $N^6$-methyl-adenine, $N^6$-tert-butyl-benzyl-adenine, imidazole, substituted imidazoles, 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil (i.e., thymine), uracil-5-oxyacetic acidmethylester, 3-(3-amino-3-N-2-carboxypropyl) uracil, (acp3)w, 2,6-diaminopurine, and 5-propynyl pyrimidine. Other examples of modified, non-standard, or derivatized base moieties may be found in U.S. Pat. Nos. 6,001,611; 5,955,589; 5,844,106; 5,789,562; 5,750,343; 5,728,525; and 5,679,785, each of which is incorporated herein by reference in its entirety.

Furthermore, a nucleic acid, polynucleotide or oligonucleotide can comprise one or more modified sugar moieties including, but not limited to, arabinose, 2-fluoroarabinose, xylulose, and a hexose.

3. Detailed Embodiments

In a first aspect, the invention provides for a method of predicting a predisposition for stroke in an individual without hypertension, the method comprising
  a) detecting in a sample from the individual the presence or absence of an allele comprising at least one polymorphism in the PDE4D locus, wherein the presence of the allele is associated with a predisposition for stroke in individuals without hypertension; and
  b) predicting the presence or absence of a predisposition for stroke in the person based on the presence or absence of the allele in the sample, wherein the presence of the allele is associated with a predisposition for stroke in individuals without hypertension. In one embodiment, the polymorphism is not predictive for stroke in individuals with hypertension. In one embodiment, the polymorphism is independently predictive for stroke in individuals with hypertension. In some embodiments, the methods are predictive of ischemic stroke, carotid stroke, cardiogenic stroke, cardioembolic stroke, small vessel stroke or large vessel stroke.

In some embodiments, the at least one polymorphism is selected from the group consisting of:

SNP 9 A/G, wherein the presence of A is associated with a predisposition for stroke;

SNP 219 C/T, wherein the presence of T is associated with a predisposition for stroke;

SNP 42 A/G, wherein the presence of G is associated with a predisposition for stroke;

SNP 220 C/A, wherein the presence of A is associated with a predisposition for stroke; and microsatellite repeats (TCAT) in AC008818-1, wherein the presence of 9 microsatellite repeats (TCAT) is associated with a predisposition for stroke.

In a further embodiment, the at least one polymorphism comprises a combination of SNP 45 G/A and microsatellite repeats (TCAT) in AC008818-1, wherein the presence of 9 microsatellite repeats (TCAT) is associated with a predisposition for stroke. In a further embodiment, the at least one polymorphism is selected from the group consisting of SNP 9 A/G, SNP 26, A/G, SNP 32 C/T, SNP 34 C/A, SNP 42 A/G, SNP 45 G/A, SNP 56 T/A, SNP 148 A/G, SNP 175 T/C, SNP 199 A/G, SNP 219 C/T, SNP 220 C/A, SNP 222 A/G, and the number of microsatellite repeats (TCAT) within AC008818-1, for example, 8 microsatellite repeats (TCAT) within AC008818-1 (i.e., allele −8), 9 microsatellite repeats (TCAT) within AC008818-1 (i.e., allele −4), 10 microsatellite repeats (TCAT) within AC008818-1 (i.e., allele 0), 11 microsatellite repeats (TCAT) within AC008818-1 (i.e., allele 4), 12 microsatellite repeats (TCAT) within AC008818-1 (i.e., allele 8), or 13 microsatellite repeats (TCAT) within AC008818-1 (i.e., allele 12).

In some embodiments, the detecting step comprises detecting at least one allele comprising a polymorphism selected from the group consisting of a single nucleotide polymorphism (SNP) of SNP 9 A/G; SNP 42 A/G; SNP 219 C/T; SNP 220 C/A; and 9, 10 or 12 microsatellite repeats (TCAT) within AC008818-1; and the predicting step comprises predicting a predisposition for stroke if at least one of the following polymorphisms is present:

SNP 9 A/G, wherein the presence of A is associated with a predisposition for stroke;

SNP 219 C/T, wherein the presence of T is associated with a predisposition for stroke;

SNP 42 A/G, wherein the presence of G is associated with a predisposition for stroke;

SNP 220 C/A, wherein the presence of A is associated with a predisposition for stroke; and microsatellite repeats (TCAT) within AC008818-1, wherein the presence of 9 microsatellite repeats (TCAT) are associated with a predisposition for stroke.

In a further embodiment, the detecting step comprises detecting a combination of SNP 45 G/A and microsatellite repeats (TCAT) within AC008818-1, wherein the presence of 9 microsatellite repeats (TCAT) is associated with a predisposition for stroke. In a further embodiment, the detecting step comprises detecting at least one polymorphism selected from the group consisting of SNP 9 A/G, SNP 26, A/G, SNP 32 C/T, SNP 34 C/A, SNP 42 A/G, SNP 45 G/A, SNP 56 T/A, SNP 148 A/G, SNP 175 T/C, SNP 199 A/G, SNP 219 C/T, SNP 220 C/A, SNP 222 A/G, and the number of microsatellite repeats (TCAT) within AC008818-1, for example, 8 microsatellite repeats (TCAT) within AC008818-1 (i.e., allele −8), 9 microsatellite repeats (TCAT) within AC008818-1 (i.e., allele −4), 10 microsatellite repeats (TCAT) within AC008818-1 (i.e., allele 0), 11 microsatellite repeats (TCAT) within AC008818-1 (i.e., allele 4), 12 microsatellite repeats (TCAT) within AC008818-1 (i.e., allele 8), or 13 microsatellite repeats (TCAT) within AC008818-1 (i.e., allele 12).

As appropriate, 2, 3, 4, 5 or more polymorphisms can be concurrently detected and used to predict an individual's predisposition for stroke, typically correlated with their hypertension status.

The invention also provides methods for predicting an increased risk for stroke in an individual with hypertension. Accordingly, in another aspect, the invention provides for a method of predicting a predisposition for stroke in a person, the method comprising
  detecting in a sample from the person SNP 175 T/C of the PDE4D locus; and
  predicting the presence or absence of a predisposition for stroke in the person based on the presence or absence of an allele of the polymorphism in the sample, wherein the presence of T is associated with a predisposition for stroke in individuals with hypertension.

The invention also provides methods for predicting a decreased risk for stroke in an individual without hypertension. In another aspect, the invention provides for a method of predicting a decreased risk for stroke in a person, the method comprising
  detecting in a sample from the person microsatellite repeats (TCAT) within AC008818-1 of the PDE4D; and
  predicting the presence or absence of a decreased risk for stroke in the person based on the presence or absence of an allele of the polymorphism in the sample, wherein the presence of 10 microsatellite repeats (TCAT) is associated with a decreased risk for stroke in individuals without hypertension. In some embodiments, the presence of 10 or 12 microsatellite repeats (TCAT) is associated with a decreased risk for stroke In some embodiments, the predicting step comprises recording the presence or absence of a predisposition for stroke for the individual.

In some embodiments, the polymorphism is detected with an oligonucleotide (e.g., a primer or a probe) that distinguishes between at least two alternative alleles of the polymorphism. In some embodiments, the oligonucleotide is detectably labeled, for example, with a fluorescent moiety, a radioactive moiety, a biotin moiety. In some embodiments, the oligonucleotide is detectably labeled with a fluorescent moiety attached to the 5'-end of the oligonucleotide. In some embodiments, the oligonucleotide further comprises a quencher moiety that quenches the fluorescent moiety when the oligonucleotide is intact.

The methods are applicable to individuals who are male or female. The methods are further applicable to individuals regardless of their racial or ethnic origin. In some embodiments, the individual is Caucasian, Asian, Negro, Hispanic, Indian, Native American, or has a combination of racial or ethnic origins.

In some embodiments, the allele is additive, multiplicative, dominant, or recessive, codominant, or a combination thereof.

In a further aspect, the invention provides for a kit for predicting a predisposition for stroke in a person without hypertension, the kit comprising, a probe or primer that distinguishes between the A allele and the G allele of SNP 9 A/G; or a probe or primer that distinguishes between the C allele and the T allele of SNP 219 C/T; or a probe or primer that distinguishes between the C allele and the A allele of SNP 220 C/A.

Typically, the probe or primer distinguishes between polymorphism alleles in a polymerase dependent reaction, for example, polymerase chain reaction (PCR) or a primer extension reaction. The selective amplification of one allele of a polymorphism can be detected concurrently with an amplification reaction (i.e., "real-time") or subsequently to an amplification reaction. In some embodiments, the probe or primer distinguishes between polymorphism alleles in a polymerase independent reaction, for example, an invasive cleavage reaction (see, for example, Olivier, *Mut. Res.* (2005) 573(1-2): 103-10).

In some embodiments, the kits further comprise one or more additional probes or primers that distinguish between PDE4D alleles. In some embodiments, the kits further comprise: a probe or primer that distinguishes between the A allele and the G allele of SNP 42 A/G; or a probe or primer that distinguishes the number of microsatellite repeats (TCAT) within AC008818-1.

In a further aspect, the invention provides for a kit for predicting a predisposition for stroke in a person with hypertension, the kit comprising, a probe or primer that distinguishes between the T allele and the C allele of SNP 175 T/C.

In some embodiments, the kits of the invention further comprise a thermostable polymerase. In some embodiments, the kits further comprises deoxynucleotides. In some embodiments the probe of the kits is detectably-labeled. In some embodiments, the probe of the kits is detectably-labeled with a fluorescent moiety. In some embodiments, the fluorescent moiety is at the 5'-end of the probe. In some embodiments, the probe of the kits further comprises a quencher moiety that quenches the fluorescent moiety when the probe is intact.

In a further aspect, the invention provides for a computer program product for use in predicting a predisposition for stroke in an individual, the computer program product comprising:

a computer readable medium encoded with program code, the program code comprising:
computer code for receiving, at a host computer, information indicating the presence of an allele of a polymorphism of the PDE4D locus associated with a predisposition for stroke in an individual, wherein the polymorphisms are selected from the group consisting of SNP 9 A/G, SNP 219 C/T, SNP 42 A/G, SNP 220 C/A, microsatellite repeats (TCAT) within AC008818-1, and SNP 175 T/C; and
computer code for determining a predisposition for stroke in the individual, wherein a predisposition for stroke is predicted if the individual has:
an A in SNP 9 A/G;
a T in SNP 219 C/T;
a G in SNP 42 A/G;
a A in SNP 220 C/A;
9 microsatellite repeats (TCAT) within AC008818-1; or
a T in SNP 175 T/C.

In a further aspect, the invention provides for a computer-implemented method for determining a predisposition for stroke in individuals, the method comprising:

receiving, at a host computer, information indicating the presence of an allele of a polymorphism of the PDE4D locus associated with a predisposition for stroke in an individual, wherein the polymorphisms are selected from the group consisting of SNP 9 A/G, SNP 219 C/T, SNP 42 A/G, SNP 220 C/A, microsatellite repeats (TCAT) within AC008818-1, and SNP 175 T/C; and
determining a predisposition for stroke in the individual, wherein a predisposition for stroke is predicted if the individual has:
an A in SNP 9 A/G;
a T in SNP 219 C/T;
a G in SNP 42 A/G;
a A in SNP 220 C/A;
9 microsatellite repeats (TCAT) within AC008818-1; or
a T in SNP 175 T/C.

In some embodiments, the computer-implemented method further comprises the step of outputting the presence or absence of a predisposition of stroke for the individual.

As appreciated by one of skill in the art, the methods of the present invention can be used in conjunction with other analyses to detect a propensity for stroke in addition to presence or absence of hypertension, including but not limited to, gender, race, ethnic origin, age, body mass index, waist:hip ratio, blood pressure, cholesterol, serum lipids, including high density lipoprotein and/or low density lipoprotein, high-sensitivity C-reactive protein (hsCRP) serum levels, presence or absence of diabetes, whether the individual smokes, exercises, etc. In some embodiments, for example, if a patient exhibits additional risk factors for incidence of stroke, the method can comprise an additional step of evaluating one or more of, for example, age, diabetes, smoking, or any of the above listed risk factors or others. Females, males or undivided populations can be analyzed for the presence of the polymorphism. Analysis can be performed at any age. The allelic frequencies may vary between particular populations.

4. Detection of Nucleic Acid Polymorphisms

Detection techniques for evaluating nucleic acids for the presence of a SNP involve procedures well known in the field of molecular genetics. Many, but not all, of the methods involve amplification of nucleic acids. Ample guidance for performing amplification is provided in the art. Exemplary references include manuals such as PCR Technology: *Principles and Applications for DNA Amplification* (ed. H. A. Erlich, Freeman Press, NY, N.Y., 1992); *PCR Protocols: A Guide to Methods and Applications* (eds. Innis, et al., Academic Press, San Diego, Calif., 1990); Current Protocols in Molecular Biology, Ausubel, 1994-1999, including supplemental updates through April 2004; Sambrook & Russell, *Molecular Cloning, A Laboratory Manual* (3rd Ed, 2001). General methods for detection of single nucleotide polymorphisms is disclosed in *Single Nucleotide Polymorphisms: Methods and Protocols*, Pui-Yan Kwok, ed., 2003, Humana Press.

Although the methods typically employ PCR steps, other amplification protocols may also be used. Suitable amplification methods include ligase chain reaction (see, e.g., Wu & Wallace, *Genomics* 4:560-569, 1988); strand displacement assay (see, e.g. Walker et al., *Proc. Natl. Acad. Sci.* USA 89:392-396, 1992; U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., *Proc. Natl. Acad. Sci.* USA 86:1173-1177, 1989); and self-sustained sequence replication (3SR) (Guatelli et al., *Proc. Natl. Acad. Sci.* USA 87:1874-1878, 1990; WO 92/08800). Alternatively, methods that amplify the probe to detectable levels can be used, such as Qβ-replicase amplification (Kramer & Lizardi, *Nature* 339:401-402, 1989; Lomeli et al., *Clin. Chem.* 35:1826-1831, 1989). A review of known amplification methods is provided, for example, by Abramson and Myers in *Current Opinion in Biotechnology* 4:41-47, 1993.

Detection of the PDE4D genotype, haplotype, SNP, microsatellite or other polymorphism of an individual can be performed using oligonucleotide primers and/or probes. Oligonucleotides can be prepared by any suitable method, usually chemical synthesis. Oligonucleotides can be synthesized using commercially available reagents and instruments. Alternatively, they can be purchased through commercial sources. Methods of synthesizing oligonucleotides are well known in the art (see, e.g, Narang et al., *Meth. Enzymol.* 68:90-99, 1979; Brown et al., *Meth. Enzymol.* 68:109-151, 1979; Beaucage et al., *Tetrahedron Lett.* 22:1859-1862, 1981; and the solid support method of U.S. Pat. No. 4,458,066). In addition, modifications to the above-described methods of synthesis may be used to desirably impact enzyme behavior with respect to the synthesized oligonucleotides. For example, incorporation of modified phosphodiester linkages (e.g., phosphorothioate, methylphosphonates, phosphoamidate, or boranophosphate) or linkages other than a phosphorous acid derivative into an oligonucleotide may be used to prevent cleavage at a selected site. In addition, the use of 2'-amino modified sugars tends to favor displacement over digestion of the oligonucleotide when hybridized to a nucleic acid that is also the template for synthesis of a new nucleic acid strand.

The genotype of an individual for PDE4D polymorphisms can be determined using many detection methods that are well known in the art. Most assays entail one of several general protocols: hybridization using allele-specific oligonucleotides, primer extension, allele-specific ligation, sequencing, or electrophoretic separation techniques, e.g., single-stranded conformational polymorphism (SSCP) and heteroduplex analysis. Exemplary assays include 5'-nuclease assays, template-directed dye-terminator incorporation, molecular beacon allele-specific oligonucleotide assays, single-base extension assays, and SNP scoring by real-time pyrophosphate sequences. Analysis of amplified sequences can be performed using various technologies such as microchips, fluorescence polarization assays, and matrix-assisted laser desorption ionization (MALDI) mass spectrometry. Two methods that can also be used are assays based on invasive cleavage with Flap nucleases and methodologies employing padlock probes.

Determination of the presence or absence of a particular PDE4D allele is generally performed by analyzing a nucleic acid sample that is obtained from the individual to be analyzed. Often, the nucleic acid sample comprises genomic DNA. The genomic DNA is typically obtained from blood samples, but may also be obtained from other cells or tissues.

It is also possible to analyze RNA samples for the presence of polymorphic alleles. For example, mRNA can be used to determine the genotype of an individual at one or more PDE4D polymorphic sites. In this case, the nucleic acid sample is obtained from cells in which the target nucleic acid is expressed, e.g., adipocytes. Such an analysis can be performed by first reverse-transcribing the target RNA using, for example, a viral reverse transcriptase, and then amplifying the resulting cDNA; or using a combined high-temperature reverse-transcription-polymerase chain reaction (RT-PCR), as described in U.S. Pat. Nos. 5,310,652; 5,322,770; 5,561,058; 5,641,864; and 5,693,517.

Frequently used methodologies for analysis of nucleic acid samples to detect SNPs are briefly described. However, any method known in the art can be used in the invention to detect the presence of single nucleotide substitutions.

a. Allele-Specific Hybridization

This technique, also commonly referred to as allele specific oligonucleotide hybridization (ASO) (e.g., Stoneking et al., *Am. J. Hum. Genet*. 48:70-382, 1991; Saiki et al., *Nature* 324, 163-166, 1986; EP 235,726; and WO 89/11548), relies on distinguishing between two DNA molecules differing by one base by hybridizing an oligonucleotide probe that is specific for one of the variants to an amplified product obtained from amplifying the nucleic acid sample. This method typically employs short oligonucleotides, e.g. 15-20 bases in length. The probes are designed to differentially hybridize to one variant versus another. Principles and guidance for designing such probe is available in the art, e.g. in the references cited herein. Hybridization conditions should be sufficiently stringent that there is a significant difference in hybridization intensity between alleles, and producing an essentially binary response, whereby a probe hybridizes to only one of the alleles. Some probes are designed to hybridize to a segment of target DNA such that the polymorphic site aligns with a central position (e.g., in a 15-base oligonucleotide at the 7 position; in a 16-based oligonucleotide at either the 8 or 9 position) of the probe, but this design is not required.

The amount and/or presence of an allele is determined by measuring the amount of allele-specific oligonucleotide that is hybridized to the sample. Typically, the oligonucleotide is labeled with a label such as a fluorescent label. For example, an allele-specific oligonucleotide is applied to immobilized oligonucleotides representing PDE4D SNP sequences. After stringent hybridization and washing conditions, fluorescence intensity is measured for each SNP oligonucleotide.

In one embodiment, the nucleotide present at the polymorphic site is identified by hybridization under sequence-specific hybridization conditions with an oligonucleotide probe or primer exactly complementary to one of the polymorphic alleles in a region encompassing the polymorphic site. The probe or primer hybridizing sequence and sequence-specific hybridization conditions are selected such that a single mismatch at the polymorphic site destabilizes the hybridization duplex sufficiently so that it is effectively not formed. Thus, under sequence-specific hybridization conditions, stable duplexes will form only between the probe or primer and the exactly complementary allelic sequence. Thus, oligonucleotides from about 10 to about 35 nucleotides in length, usually from about 15 to about 35 nucleotides in length, which are exactly complementary to an allele sequence in a region which encompasses the polymorphic site are within the scope of the invention.

In an alternative embodiment, the nucleotide present at the polymorphic site is identified by hybridization under sufficiently stringent hybridization conditions with an oligonucleotide substantially complementary to one of the SNP alleles in a region encompassing the polymorphic site, and exactly complementary to the allele at the polymorphic site. Because mismatches which occur at non-polymorphic sites are mismatches with both allele sequences, the difference in the number of mismatches in a duplex formed with the target allele sequence and in a duplex formed with the corresponding non-target allele sequence is the same as when an oligonucleotide exactly complementary to the target allele sequence is used. In this embodiment, the hybridization conditions are relaxed sufficiently to allow the formation of stable duplexes with the target sequence, while maintaining sufficient stringency to preclude the formation of stable duplexes with non-target sequences. Under such sufficiently stringent hybridization conditions, stable duplexes will form only between the probe or primer and the target allele. Thus, oligonucleotides from about 10 to about 35 nucleotides in length, usually from about 15 to about 35 nucleotides in length, which are substantially complementary to an allele sequence in a region which encompasses the polymorphic site, and are exactly complementary to the allele sequence at the polymorphic site, are within the scope of the invention.

The use of substantially, rather than exactly, complementary oligonucleotides may be desirable in assay formats in which optimization of hybridization conditions is limited. For example, in a typical multi-target immobilized-oligonucleotide assay format, probes or primers for each target are immobilized on a single solid support. Hybridizations are carried out simultaneously by contacting the solid support with a solution containing target DNA. As all hybridizations are carried out under identical conditions, the hybridization conditions cannot be separately optimized for each probe or primer. The incorporation of mismatches into a probe or primer can be used to adjust duplex stability when the assay format precludes adjusting the hybridization conditions. The effect of a particular introduced mismatch on duplex stability is well known, and the duplex stability can be routinely both estimated and empirically determined, as described above. Suitable hybridization conditions, which depend on the exact size and sequence of the probe or primer, can be selected empirically using the guidance provided herein and well known in the art. The use of oligonucleotide probes or primers to detect single base pair differences in sequence is described in, for example, Conner et al., 1983, Proc. Natl. Acad. Sci. USA 80:278-282, and U.S. Pat. Nos. 5,468,613 and 5,604,099, each incorporated herein by reference.

The proportional change in stability between a perfectly matched and a single-base mismatched hybridization duplex depends on the length of the hybridized oligonucleotides. Duplexes formed with shorter probe sequences are destabilized proportionally more by the presence of a mismatch. Oligonucleotides between about 15 and about 35 nucleotides in length are often used for sequence-specific detection. Furthermore, because the ends of a hybridized oligonucleotide undergo continuous random dissociation and re-annealing due to thermal energy, a mismatch at either end destabilizes the hybridization duplex less than a mismatch occurring internally. For discrimination of a single base pair change in target sequence, the probe sequence is selected which hybridizes to the target sequence such that the polymorphic site occurs in the interior region of the probe.

The above criteria for selecting a probe sequence that hybridizes to a specific PDE4D allele apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe.

Suitable assay formats for detecting hybrids formed between probes and target nucleic acid sequences in a sample are known in the art and include the immobilized target (dot-blot) format and immobilized probe (reverse dot-blot or line-blot) assay formats. Dot blot and reverse dot blot assay formats are described in U.S. Pat. Nos. 5,310,893; 5,451,512; 5,468,613; and 5,604,099; each incorporated herein by reference.

In a dot-blot format, amplified target DNA is immobilized on a solid support, such as a nylon membrane. The membrane-target complex is incubated with labeled probe under suitable hybridization conditions, unhybridized probe is removed by washing under suitably stringent conditions, and the membrane is monitored for the presence of bound probe.

In the reverse dot-blot (or line-blot) format, the probes are immobilized on a solid support, such as a nylon membrane or a microtiter plate. The target DNA is labeled, typically during amplification by the incorporation of labeled primers. One or both of the primers can be labeled. The membrane-probe complex is incubated with the labeled amplified target DNA under suitable hybridization conditions, unhybridized target DNA is removed by washing under suitably stringent conditions, and the membrane is monitored for the presence of bound target DNA. A reverse line-blot detection assay is described in the example.

An allele-specific probe that is specific for one of the polymorphism variants is often used in conjunction with the allele-specific probe for the other polymorphism variant. In some embodiments, the probes are immobilized on a solid support and the target sequence in an individual is analyzed using both probes simultaneously. Examples of nucleic acid arrays are described by WO 95/11995. The same array or a different array can be used for analysis of characterized polymorphisms. WO 95/11995 also describes subarrays that are optimized for detection of variant forms of a pre-characterized polymorphism. Such a subarray can be used in detecting the presence of the PDE4D polymorphisms described herein.

b. Allele-Specific Primers

Polymorphisms are also commonly detected using allele-specific amplification or primer extension methods. These reactions typically involve use of primers that are designed to specifically target a polymorphism via a mismatch at the 3'-end of a primer. The presence of a mismatch effects the ability of a polymerase to extend a primer when the polymerase lacks error-correcting activity. For example, to detect an allele sequence using an allele-specific amplification- or extension-based method, a primer complementary to one allele of a polymorphism is designed such that the 3'-terminal nucleotide hybridizes at the polymorphic position. The presence of the particular allele can be determined by the ability of the primer to initiate extension. If the 3'-terminus is mismatched, the extension is impeded.

In some embodiments, the primer is used in conjunction with a second primer in an amplification reaction. The second primer hybridizes at a site unrelated to the polymorphic position. Amplification proceeds from the two primers leading to a detectable product signifying the particular allelic form is present. Allele-specific amplification- or extension-based methods are described in, for example, WO 93/22456; U.S. Pat. Nos. 5,137,806; 5,595,890; 5,639,611; and U.S. Pat. No. 4,851,331.

Using allele-specific amplification-based genotyping, identification of the alleles requires only detection of the presence or absence of amplified target sequences. Methods for the detection of amplified target sequences are well known in the art. For example, gel electrophoresis and probe hybridization assays described are often used to detect the presence of nucleic acids.

In an alternative probe-less method, the amplified nucleic acid is detected by monitoring the increase in the total amount of double-stranded DNA in the reaction mixture, is described, e.g. in U.S. Pat. No. 5,994,056; and European Patent Publication Nos. 487,218 and 512,334. The detection of double-stranded target DNA relies on the increased fluorescence various DNA-binding dyes, e.g., SYBR Green, exhibit when bound to double-stranded DNA.

As appreciated by one in the art, allele-specific amplification methods can be performed in reaction that employ multiple allele-specific primers to target particular alleles. Primers for such multiplex applications are generally labeled with distinguishable labels or are selected such that the amplification products produced from the alleles are distinguishable by size. Thus, for example, both alleles in a single sample can be identified using a single amplification by gel analysis of the amplification product.

As in the case of allele-specific probes, an allele-specific oligonucleotide primer may be exactly complementary to one of the polymorphic alleles in the hybridizing region or may have some mismatches at positions other than the 3'-terminus of the oligonucleotide, which mismatches occur at non-polymorphic sites in both allele sequences.

c. Detectable Probes i) 5'-Nuclease Assay Probes

Genotyping can also be performed using a "TaqMan®" or "5'-nuclease assay", as described in U.S. Pat. Nos. 5,210,015; 5,487,972; and 5,804,375; and Holland et al., 1988, *Proc. Natl. Acad. Sci.* USA 88:7276-7280. In the TaqMan® assay, labeled detection probes that hybridize within the amplified region are added during the amplification reaction. The probes are modified so as to prevent the probes from acting as primers for DNA synthesis. The amplification is performed using a DNA polymerase having 5'- to 3'-exonuclease activity. During each synthesis step of the amplification, any probe which hybridizes to the target nucleic acid downstream from the primer being extended is degraded by the 5'- to 3'-exonuclease activity of the DNA polymerase. Thus, the synthesis of a new target strand also results in the degradation of a probe, and the accumulation of degradation product provides a measure of the synthesis of target sequences.

The hybridization probe can be an allele-specific probe that discriminates between the SNP alleles. Alternatively, the method can be performed using an allele-specific primer and a labeled probe that binds to amplified product.

Any method suitable for detecting degradation product can be used in a 5'-nuclease assay. Often, the detection probe is labeled with two fluorescent dyes, one of which is capable of quenching the fluorescence of the other dye. The dyes are attached to the probe, usually one attached to the 5'-terminus and the other is attached to an internal site, such that quenching occurs when the probe is in an unhybridized state and such that cleavage of the probe by the 5'- to 3'-exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated herein by reference, describe alternative methods for detecting the degradation of probe which occurs concomitant with amplification.

ii) Secondary Structure Probes

Probes detectable upon a secondary structural change are also suitable for detection of a polymorphism, including SNPs. Exemplified secondary structure or stem-loop structure probes include molecular beacons or Scorpion® primer/probes. Molecular beacon probes are single-stranded oligonucleic acid probes that can form a hairpin structure in which a fluorophore and a quencher are usually placed on the opposite ends of the oligonucleotide. At either end of the probe short complementary sequences allow for the formation of an intramolecular stem, which enables the fluorophore and the quencher to come into close proximity. The loop portion of the molecular beacon is complementary to a target nucleic acid of interest. Binding of this probe to its target nucleic acid of interest forms a hybrid that forces the stem apart. This causes a conformation change that moves the fluorophore and the quencher away from each other and leads to a more intense fluorescent signal. Molecular beacon probes are, however, highly sensitive to small sequence variation in the probe target (Tyagi S. and Kramer F. R., *Nature Biotechnology*, Vol. 14, pages 303-308 (1996); Tyagi et al., *Nature Biotechnology*, Vol. 16, pages 49-53(1998); Piatek et al., *Nature Biotechnology*, Vol. 16, pages 359-363 (1998); Marras S. et al., *Genetic Analysis: Biomolecular Engineering*, Vol. 14, pages 151-156 (1999); Tpp I. et al, *BioTechniques*, Vol 28, pages 732-738 (2000)). A Scorpion® primer/probe comprises a stem-loop structure probe covalently linked to a primer.

d. DNA Sequencing and Single Base Extensions

The PDE4D SNPs can also be detected by direct sequencing. Methods include e.g. dideoxy sequencing-based methods and other methods such as Maxam and Gilbert sequence (see, e.g. Sambrook and Russell, supra).

Other detection methods include Pyrosequencing™ of oligonucleotide-length products. Such methods often employ amplification techniques such as PCR. For example, in pyrosequencing, a sequencing primer is hybridized to a single stranded, PCR-amplified, DNA template; and incubated with the enzymes, DNA polymerase, ATP sulfurylase, luciferase and apyrase, and the substrates, adenosine 5' phosphosulfate (APS) and luciferin. The first of four deoxynucleotide triphosphates (dNTP) is added to the reaction. DNA polymerase catalyzes the incorporation of the deoxynucleotide triphosphate into the DNA strand, if it is complementary to the base in the template strand. Each incorporation event is accompanied by release of pyrophosphate (PPi) in a quantity equimolar to the amount of incorporated nucleotide. ATP sulfurylase quantitatively converts PPi to ATP in the presence of adenosine 5' phosphosulfate. This ATP drives the luciferase-mediated conversion of luciferin to oxyluciferin that generates visible light in amounts that are proportional to the amount of ATP. The light produced in the luciferase-catalyzed reaction is detected by a charge coupled device (CCD) camera and seen as a peak in a Pyrogram™. Each light signal is proportional to the number of nucleotides incorporated. Apyrase, a nucleotide degrading enzyme, continuously degrades unincorporated dNTPs and excess ATP. When degradation is complete, another dNTP is added.

Another similar method for characterizing SNPs does not require use of a complete PCR, but typically uses only the extension of a primer by a single, fluorescence-labeled dideoxyribonucleic acid molecule (ddNTP) that is complementary to the nucleotide to be investigated. The nucleotide at the polymorphic site can be identified via detection of a primer that has been extended by one base and is fluorescently labeled (e.g., Kobayashi et al, *Mol. Cell. Probes*, 9:175-182, 1995).

e. Electrophoresis

Amplification products generated using the polymerase chain reaction can be analyzed by the use of denaturing gradient gel electrophoresis. Different alleles can be identified based on the different sequence-dependent melting properties and electrophoretic migration of DNA in solution (see, e.g. Erlich, ed., *PCR Technology, Principles and Applications for DNA Amplification*, W. H. Freeman and Co, New York, 1992, Chapter 7).

Distinguishing of microsatellite polymorphisms can be done using capillary electrophoresis. Capillary electrophoresis conveniently allows identification of the number of repeats in a particular microsatellite allele. The application of capillary electrophoresis to the analysis of DNA polymorphisms is well known to those in the art (see, for example, Szantai, et al, *J Chromatogr A*. (2005) 1079(1-2):41-9; Bjorheim and Ekstrom, *Electrophoresis* (2005) 26(13):2520-30 and Mitchelson, *Mol Biotechnol*. (2003) 24(1):41-68).

f. Single-Strand Conformation Polymorphism Analysis

Alleles of target sequences can be differentiated using single-strand conformation polymorphism analysis, which identifies base differences by alteration in electrophoretic migration of single stranded PCR products, as described, e.g, in Orita et al., *Proc. Nat. Acad. Sci*. 86, 2766-2770 (1989). Amplified PCR products can be generated as described above, and heated or otherwise denatured, to form single stranded amplification products. Single-stranded nucleic acids may refold or form secondary structures which are partially dependent on the base sequence. The different electrophoretic mobilities of single-stranded amplification products can be related to base-sequence difference between alleles of target SNP detection methods often employ labeled oligonucleotides. Oligonucleotides can be labeled by incorporating a label detectable by spectroscopic, photochemical, biochemical, immunochemical, or chemical means. Useful labels include fluorescent dyes, radioactive labels, e.g. $^{32}$P, electron-dense reagents, enzyme, such as peroxidase or alkaline phosphatase, biotin, or haptens and proteins for which antisera or monoclonal antibodies are available. Labeling techniques are well known in the art (see, e.g. Current Protocols in Molecular Biology, supra; Sambrook & Russell, supra).

5. Recording a Diagnosis

The methods of the invention typically involve recording the presence of the SNPs associated with a propensity for stroke. This information may be stored in a computer readable form or on paper, as appropriate. Such a computer system typically comprises major subsystems such as a central processor, a system memory (typically RAM), an input/output (I/O) controller, an external device such as a display screen via a display adapter, serial ports, a keyboard, a fixed disk drive via a storage interface and a floppy disk drive operative to receive a floppy disc, and a CD-ROM (or DVD-ROM) device operative to receive a CD-ROM. Many other devices can be connected, such as a network interface connected via a serial port.

The computer system can also be linked to a network, comprising a plurality of computing devices linked via a data link, such as an Ethernet cable (coax or 10BaseT), telephone line, ISDN line, wireless network, optical fiber, or other suitable signal transmission medium, whereby at least one network device (e.g., computer, disk array, etc.) comprises a pattern of magnetic domains (e.g., magnetic disk) and/or charge domains (e.g., an array of DRAM cells) composing a bit pattern encoding data acquired from an assay of the invention.

The computer system can comprise code for interpreting the results of a genotype study evaluating one or more PDE4D polymorphic alleles. Thus in an exemplary embodiment, the genotype results are provided to a computer where a central processor executes a computer program for determining the propensity for an increased or decreased predisposition of stroke.

The invention also provides the use of a computer system, such as that described above, which comprises: (1) a computer; (2) a stored bit pattern encoding the genotyping results obtained by the methods of the invention, which may be stored in the computer; (3) and, optionally, (4) a program for determining the predisposition for stroke.

6. Kits

The invention also provides kits comprising useful components for practicing the methods. In some embodiments, the kit may comprise one or more allele-specific detection probes, which optionally can be fixed to an appropriate support membrane. Such a kit can also contain one or more amplification primers for amplifying a region of the PDE4D locus encompassing the one or more polymorphic sites. Alternatively, useful kits can contain one or more sets of primers comprising an allele-specific primer for the specific amplification of the polymorphic alleles. Such a kit may also comprises probes for the detection of amplification products.

Other optional components of the kits include additional reagents used for genotyping patients. For example, a kit can contain a polymerase, substrate nucleoside triphosphates, means for labeling and/or detecting nucleic acid (for example, an avidin-enzyme conjugate and enzyme substrate and chromogen if the label is biotin), appropriate buffers for amplification or hybridization reactions, and instructions for carrying out the present methods.

As appropriate, the kits can comprise multiple probes or primers for detecting 2, 3, 4, 5 or more polymorphisms. For example, the kits can include probes or primers for detecting or distinguishing at least one polymorphism selected from the group consisting of SNP 9 A/G, SNP 26, A/G, SNP 32 C/T, SNP 34 C/A, SNP 42 A/G, SNP 45 G/A, SNP 56 T/A, SNP 148 A/G, SNP 175 T/C, SNP 199 A/G, SNP 219 C/T, SNP 220 C/A, SNP 222 A/G, and the number of microsatellite repeats (TCAT) within AC008818-1, for example, 8 microsatellite repeats (TCAT) within AC008818-1 (i.e., allele −8), 9 microsatellite repeats (TCAT) within AC008818-1 (i.e., allele −4), 10 microsatellite repeats (TCAT) within AC008818-1 (i.e., allele 0), 11 microsatellite repeats (TCAT) within AC008818-1 (i.e., allele 4), 12 microsatellite repeats (TCAT) within AC008818-1 (i.e., allele 8), or 13 microsatellite repeats (TCAT) within AC008818-1 (i.e., allele 12). In some embodiments, a kit will include probes or primers to detect or distinguish at least one polymorphism selected from the group consisting of SNP 9 A/G, SNP 42 A/G, SNP 219 C/T and SNP 220 C/A. In other embodiments, a kit will include probes or primers for distinguishing the alleles of SNP 175. In other embodiments, a kit will include probes or primers for distinguishing polymorphisms of microsatellite repeats (TCAT) within AC008818-1.

7. Association Testing

One or more of several models of association testing can be applied to statistically correlating the presence or absence of one or more PDE4D polymorphisms with stroke, the presence or absence of hypertension, and optionally, one or more additional risk factors. Exemplified genetic models include, but are not limited to, dominant, recessive, codominant, allelic/multiplicative/additive.

An allelic/multiplicative/additive (logit scale) model describes disease risk conferred by a particular allele in comparison to a reference allele (usually the most common variant).

A dominant genetic model describes disease risk of individuals carrying one or two copies of an allele (usually the minor, or rare, variant) compared to those with none.

A recessive genetic model describes disease risk of individuals carrying exactly two copies of an allele (usually the minor, or rare, variant) compared to those with either one or no copies of the allele.

A codominant genetic model treats each genotypes as conferring distinct disease risk.

EXAMPLE

The following example is offered to illustrate, but not to limit the claimed invention.

Example 1

Identification and Detection of PDE4D SNPs Predictive of Stroke in Individuals with or without Hypertension Materials and Methods Subjects The Study of Osteoporotic Fractures (SOF) (see, Browner, et al., *J Clin Endocrinol Metab* (2001) 86:631-637) recruited ambulatory women between 1986 and 1988 from four clinical centers in Portland, Oreg.; Minneapolis, Minn.; Baltimore, Md.; and the Monongahela Valley, Pa. (Cummings, et al., *JAMA* (1990) 263:665-668). The study group consists of 9704 white women of at least 65 years of age who had not had bilateral hip replacement or earlier hip fracture at the time of recruitment. Cases of stroke suffered incident adjudicated ischemic strokes (Browner, et al., supra) (N=248). Controls did not experience a stroke prior to study recruitment or during a mean follow-up of 5.4 years (N=560). Hypertension was defined at baseline as systolic blood pressure (BP)>160 mm Hg or diastolic BP>90 mm Hg or the use of thiazide diuretics. Individuals who died during follow-up were included. The study was approved by the institutional review boards and all women provided written informed consent.

The Icelandic population has been described previously (Gretarsdottir, et al., *Nature Genetics* (2003) 35(2):131-138). For comparison with SOF stroke, some results not presented in Gretarsdottir et al. are summarized in Tables 2 and 3.

TABLE 2

Table 2. Minor allele frequencies and unadjusted associations in SOF stroke and in the Iceland stroke population using an allelic model. P values <0.05 are in bold.

| Region | SNP | SOF Stroke | | | | Iceland Stroke | | | |
| --- | --- | --- | --- | --- | --- | --- | --- | --- | --- |
| | | Control Allele Freq. | Case Allele Freq. | P-Value | HR | Control Allele Freq. | Case Allele Freq. | P-Value | RR |
| A | SNP 9 A/G | 0.110 | 0.087 | 0.09 | 0.75 | 0.086 | 0.093 | 0.7 | 1.54 |
| | SNP 26 A/G | 0.414 | 0.432 | 0.65 | 1.06 | 0.441 | 0.436 | 0.43 | 0.91 |
| | SNP 32 C/T | 0.412 | 0.399 | 0.94 | 0.99 | 0.295 | 0.379 | 0.00024 | 1.46 |
| | SNP 34 C/A | 0.413 | 0.399 | 0.97 | 1.00 | 0.365 | 0.381 | 0.25 | 1.10 |
| | SNP 42 A/G | 0.358 | 0.405 | 0.72 | 1.05 | 0.363 | 0.314 | 0.012 | 0.67 |
| | SNP 45 G/A | 0.149 | 0.158 | 0.50 | 0.91 | 0.22 | 0.176 | 0.0065 | 0.75 |
| | SNP 56 T/A | 0.333 | 0.350 | 0.98 | 1.00 | 0.345 | 0.286 | 0.0028 | 0.76 |
| D | SNP 148 A/G | 0.375 | 0.390 | 0.31 | 0.88 | 0.399 | 0.417 | 0.3 | 1.08 |
| | SNP 175 T/C | 0.291 | 0.276 | 0.73 | 0.96 | 0.272 | 0.248 | 0.18 | 0.88 |
| | SNP 199 A/G | 0.305 | 0.284 | 0.67 | 0.95 | 0.299 | 0.299 | 0.99 | 1.00 |
| | SNP 219 C/T | 0.353 | 0.389 | 0.15 | 1.20 | 0.468 | 0.44 | 0.174 | 0.89 |
| | SNP 220 C/A | 0.143 | 0.167 | 0.12 | 1.25 | 0.2 | 0.191 | 0.57 | 0.94 |
| | SNP 222 A/G | 0.320 | 0.317 | 0.15 | 1.20 | 0.366 | 0.337 | 0.11 | 0.88 |

SNP 9 controls are out of HWE (Exact P = 0.048)
SNP 222 cases are out of HWE (Exact P = 0.024)

TABLE 3

Table 3. Stroke-associated estimated haplotypes in the SOF and Iceland populations. Haplotypes with P values <0.05 and allele frequency of at least 1% in both groups are shown.

| Region | Stratification | Haplotype | Population | Control Frequency | Case Frequency | OR | P-Value |
|---|---|---|---|---|---|---|---|
| A | none | AATAA | Iceland | 0.12 | 0.19 | 1.8* | 0.00002 |
|   |      | GATAA | SOF     | 0.095 | 0.066 | 0.67 | 0.048 |
|   | -htn | GATAA | SOF     | 0.097 | 0.044 | 0.43 | 0.015 |
| D | none | GTACCA | Iceland | 0.126 | 0.170 | 1.42* | 0.004 |
|   |      | GTATAG | SOF     | 0.016 | 0.046 | 2.96 | 0.0006 |
|   | -htn | GTATAG | SOF     | 0.019 | 0.049 | 2.63 | 0.012 |
|   |      | GTATCA | SOF     | 0.022 | 0.050 | 2.29 | 0.033 |
|   |      | ATATCG | SOF     | 0.044 | 0.015 | 0.32 | 0.048 |
|   | +htn | GTATAG | SOF     | 0.014 | 0.053 | 3.86 | 0.006 |

A region haplotype SNPs, in order: SNP9-26-32-34-42
D region haplotype SNPs, in order: SNP148-175-199-219-220-222
*reported as RR; Iceland Cases = 988, Controls = 652

Genotyping

Genotypes for microsatellite repeats (TCAT) within AC008818-1 were generated using Applied Biosystems (AB) Genescan® and Genotyper® software, following allele determination by fragment sizing capillary electrophoresis on an AB 3100 Genetic Analyzer. Eight SNPs were genotyped using allele-specific real-time PCR (i.e., kinetic thermal cycling) and detection by SYBR™ Green (Molecular Probes, Eugene, Oreg.) on an AB 5700 (Applied Biosystems, Foster City, Calif.) using a modification of Germer et al. (*Genome Res* (2000) 10:258-266). The samples underwent extensive quality control.

Five SNPs were genotyped by an immobilized probe-based assay. We have developed multi-target genotyping assays for candidate markers within genes from various pathways implicated in atherosclerotic and thrombotic disease, including SNPs in the Phosphodiesterase (PDE4D) gene (Cheng, et al., *Genome Res* (1999) 9:936-949; and Burns, et al., *Genes Immun* (2005) 6(5):438-444). Briefly, 15 ng of genomic DNA were amplified in a multiplex PCR with 5'-biotinylated primers and the PCR products hybridized to a linear array of immobilized oligonucleotide sequence-specific probes. Detection was carried out by HRP-mediated colorimetry. SNP nomenclature is as described in Supplementary Table 2 in Gretarsdottir et al. (Gretarsdottir, et al., (2003), supra).

Primers and Probes

The following primers and probes were used in the present study.

Linear Array Primers (SNPs)

| SNP | Primer Name | Primer Sequence | SEQ ID NO: |
|---|---|---|---|
| 9 | PDE4D120FB | EAATGAGAGTACAACATTTCAACATATTACCA | 20 |
| 9 | PDE4D121RB | EGAGTTTCGTTGTTTTAGATGCATCTCA | 21 |
| 26 | PDE4D118FB | ECAGAAGCTGTGGGCATGCAA | 22 |
| 26 | PDE4D119RB | EGAGTTCCCCCTCCAATGCTAAGA | 23 |
| 32 | PDE4D116FB | ETCATAGTGGCTGTAGTGACTGGTTGA | 24 |
| 32 | PDE4D117RB | EGCAGGCATTTGGAAATGGGA | 25 |
| 34 | PDE4D114RB | ECACAATTCTGGCCTTTTGGGA | 26 |
| 34 | PDE4D115RB | EAAGGACCCTTGCCAAAGGTGA | 27 |
| 42 | PDE4D112FB | ETCTCATTACCTAGAAGAGTTTTGACTGCA | 28 |
| 42 | PDE4D113RB | ETTATTGTTTAAATTAATCTTCCTAAGGCCA | 29 |
| 45 | PDE4D172FB | EGGGGACAGGGGTACACAGCA | 30 |
| 45 | PDE4D173RB | ETCAATTGGCTGCAGATTACAGTGAA | 31 |
| 56 | PDE4D174FB | ETTGCTCAAAGATCTTCAATGAATCTTGA | 32 |
| 56 | PDE4D175RB | ETTAGGAAGTAGTGGGACCAGGATCAA | 33 |
| 148 | PDE4D78FB | ETGTCTATACTGGCTGTTTGTCTGTCA | 34 |
| 148 | PDE4D79RB | EGATTGGAATGAAGATCATTGAAGTACA | 35 |
| 175 | PDE4D72FB | ECATGAAGCATATTTAAGGAATGATAACAGTCTA | 36 |
| 175 | PDE4D73RB | ETTCTCTTGGAATCTCAACAGTTCTGA | 37 |
| 199 | PDE4D65FB | ETTTTCTTGTTTATGTTTGTGTTTTCATGTTA | 38 |
| 199 | PDE4D66RB | EACATGTCATATCATACACCATTTTGTAAAT | 39 |
| 219 | PDE4D59FB | ETGATATGTAAGTACAAGGGCAGGCA | 40 |
| 219 | PDE4D81RB | EAGTGACAGTGCACTCAGGTTAAATCTA | 41 |
| 220 | PDE4D53FB | EGTGAGCACAATCCTTGAGGCA | 42 |
| 220 | PDE4D54RB | ECCCTTGGGTGGAAAACTCTCC | 43 |

-continued

| | | | |
|---|---|---|---|
| 222 | PDE4D47FB | ECTTCTGGTGATAATTTGGGACATCA | 44 |
| 222 | PDE4D48RB | EACAAATGTTTAGCACATGTGTGTAGACA | 45 |

E = biotin

Linear Array Probes (SNPs)

| SNP | Probe Name | Probe Sequence | SEQ ID NO: |
|---|---|---|---|
| 56 | PDE4D182RQ | JAGAGTACATGTTAATCATGTAGGAA | 46 |
| 56 | PDE4D180FQ | JTTCCTACATGTTTAACATGTACTCT | 47 |
| 45 | PDE4D178RQ | JCTCCTGTTACTGTGCCCT | 48 |
| 45 | PDE4D176FQ | JAGGGCACAATAACAGGAG | 49 |
| 42 | PDE4D92FQ | JTCACATGCATTATTAATATGATTTC | 50 |
| 42 | PDE4D94RQ | JGAAATCATACTAATAATGCATGTGA | 51 |
| 42 | PDE4D184FQ | JTCACATGCATTATTAAAATGATTTC | 52 |
| 42 | PDE4D185RQ | JGAAATCATTCTAATAATGCATGTGA | 53 |
| 34 | PDE4D99RQ | JACAAGTTGATTCCCCAGAGT | 54 |
| 34 | PDE4D142FQ | JTCTGGGGACTCAACTTGT | 55 |
| 32 | PDE4D103RQ | JCTCTAACAGCTAAGGCAACTG | 56 |
| 32 | PDE4D101RQ | JTCTAACAGCTAGGGCAACTG | 57 |
| 32 | PDE4D102RQ | JCTCTAACAGCTGAGGCAACT | 58 |
| 32 | PDE4D100FQ | JAGTTGCCCCAGCTGTTA | 59 |
| 26 | PDE4D104FQ | JCAAGAAGCAGAAGGTGAAGT | 60 |
| 26 | PDE4D106RQ | JCTTCACCTCCTGCTTCTTG | 61 |
| 9 | PDE4D148FQ | JTCTAATTCACCTATTGACTCAAAT | 62 |
| 9 | PDE4D110RQ | JTTTGAGTCAACAGGTGAATTAGA | 63 |
| 222 | PDE4D44FQ | JCTCTATTGTATTGGTTTTTATTAAACAAA | 64 |
| 222 | PDE4D46RQ | JTTGTTTAACAAAAACCAATACAATAGA | 65 |
| 219 | PDE4D158FQ | JCTCTCCTCCAATGTAGAAAGAA | 66 |
| 219 | PDE4D154RQ | JALTCTLTCTACALTGGAGAAGAG | 67 |
| 219 | PDE4D151FQ | JCTGTCCTCCAATGTAGAAAGAAT | 68 |
| 219 | PDE4D155RQ | JALTCTLTCTACALTGGAGAACAG | 69 |
| 220 | PDE4D50FQ | JATCATGTACTGCAGGAACAGAGA | 70 |
| 220 | PDE4D89RQ | JCTTTCTGTTCCTTCAGTACATGATA | 71 |
| 199 | PDE4D61FQ | JGTTTGAGAATGTAAGAATTTTAACC | 72 |
| 199 | PDE4D82RQ | JGGTTAAAATTCTCACATTCTCAAACA | 73 |
| 175 | PDE4D90FQ | JAAAGGTTAGGGACTAGTTGAATTA | 74 |
| 175 | PDE4D70RQ | JCTAATTCAACTAATCCCTAACCTTT | 75 |
| 148 | PDE4D75FQ | JCTTCCTTCCATTGGGTTTC | 76 |
| 148 | PDE4D83RQ | JTGAAACCCAACGGAAGGAAG | 77 |

J = BSA (Bovine Serum Albumin Conjugate)
L = 5-Propynyl dUTP (substitutes for T and results in stronger base-pairing

Kinetic Thermal Cycling (real-time PCR) Primers

| SNP | Primer Name | Primer Sequence | SEQ ID NO: | Primer Specificity |
|---|---|---|---|---|
| 222 | PDE4D25RK | CATGTGTGTAGACATATTCACTAAGCA | 78 | common |
| 222 | PDE4D26FKA | AAGTCTCTCTATTGTATTGGTTTTTA | 79 | A |
| 222 | PDE4D27FKG | GTCTCTCTATTGTATTGGTTTTTG | 80 | G |
| 220 | PDE4D28RK | GGGTGGAAAACTCTCCATCT | 81 | common |
| 220 | PDE4D29FK | TGAGGCATTTATCATGTACTGA | 82 | A |
| 220 | PDE4D30FKC | GAGGCATTTATCATGTACTGC | 83 | C |
| 219 | PDE4D31FK | ATGACTTTTGTTCAACTGTATCACTC | 84 | common |
| 219 | PDE4D32RKC | TCATATTCTTTCTACATTGGAGG | 85 | C |
| 219 | PDE4D33RKT | TTCATATTCTTTCTACATTGGAGA | 86 | T |
| 199 | PDE4D34RK | ACATGTCATATCATACACCATTTTGT | 87 | common |
| 199 | PDE4D35RKA | AAACAAGTTACTGTTTGAGAATGTA | 88 | A |
| 199 | PDE4D36RKG | AACAAGTTACTGTTTGAGAATGTG | 89 | G |
| 175 | PDE4D37RK | TTGGAATCTCAACAGTTCTGACTA | 90 | common |
| 175 | PDE4D38RKC | AAAATAAAATAGAAAGGTTAGGGAC | 91 | C |
| 175 | PDE4D39FKT | AAAATAAAATAGAAAGGTTAGGGAT | 92 | T |
| 148 | PDE4D40RK | GATTGGAATGAAGATCATTGAAG | 93 | common |
| 148 | PDE4D41FKA | ATGATTTTTAGCTTCCTTCCA | 94 | A |
| 148 | PDE4D42FKG | GATTTTTAGCTTCCTTCCG | 95 | G |
| 42 | PDE4D122FK | ATTTTAGAATTTTGTCACATGCATT | 96 | common |
| 42 | PDE4D123RKA | GGCCATGAATATGAAATCATAT | 97 | A |
| 42 | PDE4D124RKG | GGCCATGAATATGAAATCATAC | 98 | G |
| 34 | PDE4D125RK | AGGTGAATCCGAGCACAAGTT | 99 | common |
| 34 | PDE4D126FKA | ATGTTTTACACTCTGGGGAA | 100 | A |
| 34 | PDE4D127FKC | AATGTTTTACACTCTGGGGAC | 101 | C |
| 32 | PDE4D131FK | TTAATCTATTTCAGCCTCAGTTGC | 102 | common |
| 32 | PDE4D132RKC | GATATAATTAACCTCTAACAGCTG | 103 | C |
| 32 | PDE4D133RKT | TGATATAATTAACTCCTCTAACAGCTA | 104 | T |

-continued

| 26 | PDE4D134RK | TCTTTCCCTTCATCCACCTTTG | 105 | common |
| 26 | PDE4D135FKA | AAGTGTAGCCAAGAAGCAGA | 106 | A |
| 26 | PDE4D136FKG | GTGTAGCCAAGAAGCAGG | 107 | G |
| 45 | PDE4D166RK | GAACAAAAGTATTGCTGCCATCATT | 108 | common |
| 45 | PDE4D167FKA | ACAGCAGATAGGGCACAA | 109 | A |
| 45 | PDE4D168FKG | ACAGCAGATAGGGCACAG | 110 | G |
| 56 | PDE4D169FK | TCAATGAATCTTGATTTCTATGTGAT | 111 | common |
| 56 | PDE4D170FKT | GTCTAGCTTCAGAGTACATGTTAAA | 112 | T |
| 56 | PDE4D171FKA | AGTCTAGCTTCAGAGTACATGTTAAT | 113 | A |

Statistical Analyses

Genotype and allele frequencies were determined by counting and a Chi-square or Exact test was used to assess departure from Hardy-Weinberg equilibrium (HWE). SNPs were tested for association with incident stroke using the Cox proportional hazard model (Cox, et al., *Journal of the Royal Statistical Society* (1972) 34: 187-220). Adjusted analyses included age, weight, diabetes, and smoking as covariates. Analyses were carried out using SAS statistical software (version 8.2, SAS Institute Inc., Cary, N.C.). Pairwise linkage disequilibrium was calculated by the expectation maximization (EM) algorithm.

The association of SNP haplotypes with case/control status in the SOF sample was tested with the likelihood ratio test after haplotype frequencies were estimated by EM algorithm. SNP haplotype associations in Iceland were computed by EM algorithm as implemented in NEMO software (Gretarsdottir, et al., (2003), supra) which accounts for uncertainty in established haplotype counts.

The fourteen polymorphisms were chosen based on results obtained in the Icelandic stroke population (Tables 2 and 5, supra) and therefore were expected to be associated with stroke either as single SNPs or as a haplotype and results were not corrected for multiple comparisons.

Results

As expected, stroke cases were older than controls, and more likely to have hypertension and diabetes (Table 4). Stratification by hypertension had little effect on age, weight, or smoking distribution, although diabetes was more frequent in hypertensive subjects but had a smaller hazard ratio (HR) than in non-hypertensives (HR 2.43 versus 3.80). Two SNPs deviated modestly from HWE: SNP 9 in controls (P=0.048) and SNP 222 in cases (P=0.024). There were no significant associations between SNP alleles and incident stroke. Three polymorphisms—SNPs 9, 219, and 222—were weakly associated (P<0.10) with stroke, one each in an additive, dominant, or recessive model (Table 2, supra).

TABLE 4

Table 4. Selected characteristics of the SOF stroke cases and controls.

| | Case | | Control | | | |
|---|---|---|---|---|---|---|
| | Mean ± S.D. | N | Mean ± S.D. | N | HR | P-Value |
| Baseline age (yrs) | 73.9 ± 5.9 | 248 | 70.3 ± 4.5 | 560 | 1.59* | <0.0001 |
| Weight (kg) | 67.6 ± 12.2 | 248 | 68.1 ± 12.9 | 560 | 0.998* | 0.969 |
| Diabetes (Y/N) | 19.2% | 245 | 4.3% | 558 | 2.70 | <0.0001 |
| Hypertensive (Y/N) | 56.5% | 248 | 32.7% | 560 | 1.71 | <0.0001 |
| Smoking (Y/N) | 8.5% | 246 | 7.9% | 559 | 1.27 | 0.296 |

HR: Hazard ratio
*Per 5 years or per 10 kg

Stratification by Hypertension

After stratification by hypertension, four SNPs showed significant association (P<0.05) with stroke in women without moderate or severe hypertension (additive model SNPs 9, 42, 219, and 220; dominant model SNPs 9, 42, 219, and 220; recessive model SNP 42). SNP 175 was significantly associated with stroke in hypertensive subjects (Table 5). The data presented were adjusted for age, diabetes, smoking, and weight. Unadjusted results were very similar. Table 6 shows SOF stroke allele frequencies after stratification by hypertension status.

None of the microsatellite alleles of AC008818-1 were significantly associated with stroke in the unstratified SOF population but two alleles were significant after stratification: alleles 0 (10-repeat allele, RR 0.62, P=0.001) and −4 (9 repeats, RR 1.35, P=0.031) (Table 7).

TABLE 5

Table 5. Associations between PDE4D SNPs and stroke in SOF after stratification by hypertension and adjustment for age, diabetes, smoking, and weight. P values <0.05 are in bold.

| | Without Hypertension | | | | | | With Hypertension | | | | | |
|---|---|---|---|---|---|---|---|---|---|---|---|---|
| | Additive | | Dominant | | Recessive | | Additive | | Dominant | | Recessive | |
| SNP | P-Value | HR | P-Value | HR | P-Value | HR | P-Value | HR | P-Value | HR | P-Value | HR |
| SNP 9 A/G | 0.040 | 0.53 | 0.023 | 0.48 | 0.147 | 4.37 | 0.822 | 1.05 | 0.822 | 1.05 | — | — |
| SNP 26 A/G | 0.787 | 1.04 | 0.643 | 1.10 | 0.919 | 0.97 | 0.413 | 1.11 | 0.450 | 1.15 | 0.571 | 1.13 |
| SNP 32 C/T | 0.784 | 0.96 | 0.928 | 1.02 | 0.520 | 0.83 | 0.619 | 0.94 | 0.519 | 0.89 | 0.907 | 0.97 |

TABLE 5-continued

Table 5. Associations between PDE4D SNPs and stroke in SOF after stratification by hypertension and adjustment for age, diabetes, smoking, and weight. P values <0.05 are in bold.

| | Without Hypertension | | | | | | With Hypertension | | | | | |
|---|---|---|---|---|---|---|---|---|---|---|---|---|
| | Additive | | Dominant | | Recessive | | Additive | | Dominant | | Recessive | |
| SNP | P-Value | HR | P-Value | HR | P-Value | HR | P-Value | HR | P-Value | HR | P-Value | HR |
| SNP 34 C/A | 0.784 | 0.96 | 0.928 | 1.02 | 0.520 | 0.83 | 0.596 | 0.94 | 0.519 | 0.89 | 0.857 | 0.96 |
| SNP 42 A/G | 0.007 | 1.45 | 0.017 | 1.73 | 0.050 | 1.57 | 0.819 | 1.03 | 0.929 | 1.02 | 0.720 | 1.11 |
| SNP 45 G/A | 0.525 | 1.13 | 0.639 | 1.10 | 0.435 | 1.58 | 0.662 | 0.92 | 0.454 | 0.86 | 0.404 | 1.54 |
| SNP 56 T/A | 0.197 | 1.20 | 0.190 | 1.32 | 0.498 | 1.20 | 0.896 | 1.02 | 0.906 | 0.98 | 0.583 | 1.19 |
| SNP 148 A/G | 0.544 | 0.92 | 0.382 | 0.84 | 0.991 | 1.00 | 0.430 | 1.10 | 0.876 | 1.03 | 0.177 | 1.36 |
| SNP 175 T/C | 0.729 | 1.06 | 0.732 | 1.07 | 0.851 | 1.07 | 0.038 | 0.76 | 0.057 | 0.72 | 0.158 | 0.65 |
| SNP 199 A/G | 0.617 | 0.92 | 0.816 | 0.96 | 0.458 | 0.73 | 0.358 | 0.89 | 0.383 | 0.86 | 0.558 | 0.84 |
| SNP 219 C/T | 0.040 | 1.35 | 0.012 | 1.73 | 0.757 | 1.10 | 0.546 | 1.08 | 0.514 | 1.12 | 0.780 | 1.07 |
| SNP 220 C/A | 0.045 | 1.44 | 0.027 | 1.56 | 0.757 | 0.73 | 0.555 | 1.10 | 0.459 | 1.16 | 0.938 | 0.96 |
| SNP 222 A/G | 0.968 | 0.99 | 0.484 | 1.15 | 0.182 | 0.54 | 0.685 | 0.95 | 0.924 | 0.98 | 0.477 | 0.81 |

Without Hypertension: N cases = 108 controls = 377
With Hypertension: N cases = 139 controls = 183

TABLE 6

Allele frequencies in SOF stroke after stratification by hypertension.

| | Without Hypertension | | With Hypertension | |
|---|---|---|---|---|
| SNP | Controls | Stroke Cases | Controls | Stroke Cases |
| SNP9 A/G | 0.111 | 0.056 | 0.107 | 0.111 |
| SNP26 A/G | 0.411 | 0.403 | 0.421 | 0.454 |
| SNP32 C/T | 0.418 | 0.394 | 0.399 | 0.404 |
| SNP34 C/A | 0.418 | 0.394 | 0.402 | 0.404 |
| SNP42 A/G | 0.368 | 0.495 | 0.336 | 0.336 |
| SNP45 G/A | 0.148 | 0.187 | 0.153 | 0.136 |
| SNP56 T/A | 0.348 | 0.416 | 0.302 | 0.299 |
| SNP148 A/G | 0.38 | 0.374 | 0.366 | 0.403 |
| SNP175 T/C | 0.263 | 0.262 | 0.347 | 0.288 |
| SNP199 A/G | 0.295 | 0.278 | 0.325 | 0.288 |
| SNP219 C/T | 0.359 | 0.421 | 0.339 | 0.364 |
| SNP220 C/A | 0.155 | 0.201 | 0.118 | 0.14 |
| SNP222 A/G | 0.32 | 0.319 | 0.32 | 0.314 |

Haplotype Analysis

For comparison with Gretarsdottir et al.'s (2003, supra) results, we examined the association between the SNP 45/microsatellite haplotype and stroke. In contrast to the Icelandic results (RR 2.07, P=$7.2 \times 10^{-8}$ for G/0 relative to A/X; X=not 0 allele), the haplotype was significant only in SOF subjects without hypertension (G/0 relative to A/X, RR 0.46, P=0.003) and the association was in the opposite direction. However, the haplotype provided little improvement over the microsatellite alone in the SOF sample.

Estimated haplotypes for six SNPs in the D region and five SNPs in the A region were examined for association with stroke in the SOF sample, based on results in Iceland (Table 3, supra). The Icelandic haplotypes were not significantly associated in the SOF sample; the converse was also true (Table 3). In the A region, one haplotype, GATAA, which is the same as the Icelandic haplotype except for SNP 9 (A allele in Iceland, G allele in SOF), achieved a P value≦0.05. Additionally, the direction of association was opposite in the two populations. After stratification by hypertension, the GATAA

TABLE 7

Table 7. Microsatellite allele frequencies of AC008818-1 in the SOF stroke population. P values <0.05 are in bold.

| | | Unstratified | | | | Without Hypertension | | | | Hypertension | | | |
|---|---|---|---|---|---|---|---|---|---|---|---|---|---|
| Allele | Number of TCAT repeats | Control Freq. | Case Freq. | RR | P-Value | Control Freq. | Case Freq. | RR | P-Value | Control Freq. | Case Freq. | RR | P-Value |
| −8 | 8 | 0.164 | 0.174 | 1.06 | 0.627 | 0.164 | 0.2028 | 1.24 | 0.193 | 0.163 | 0.151 | 0.92 | 0.675 |
| −4 | 9 | 0.197 | 0.203 | 1.03 | 0.805 | 0.203 | 0.2736 | 1.35 | 0.031 | 0.185 | 0.147 | 0.79 | 0.204 |
| 0 | 10 | 0.270 | 0.234 | 0.86 | 0.120 | 0.274 | 0.1698 | 0.62 | 0.001 | 0.262 | 0.283 | 1.08 | 0.563 |
| 4 | 11 | 0.202 | 0.223 | 1.11 | 0.333 | 0.204 | 0.2264 | 1.11 | 0.488 | 0.196 | 0.221 | 1.12 | 0.452 |
| 8 | 12 | 0.158 | 0.165 | 1.04 | 0.725 | 0.144 | 0.1274 | 0.89 | 0.539 | 0.188 | 0.195 | 1.04 | 0.824 |
| 12 | 13 | 0.009 | 0.002 | 0.229 | 0.086 | 0.011 | 0.000 | 0.00 | 0.045 | 0.006 | 0.004 | 0.67 | 0.734 |

Case N = 242 Control N = 553
Allele 12 was not considered significant (Without Hypertension) due to the low frequency in the population.

haplotype remained the sole significant one (P=0.015, OR=0.43) in non-hypertensives and no haplotypes were significantly associated with stroke in hypertensives.

For region D, several haplotypes in SOF stroke showed association with a nominal P value≦0.05 but only one with frequency greater than 1% in both cases and controls (Table 3). This haplotype differed from the Icelandic haplotype at three positions but both conferred increased risk. In non-hypertensive subjects, three haplotypes had frequencies greater than 1% and P<0.05. In hypertensive subjects, one haplotype had a frequency greater than 1% and P value<0.05.

Figure 2:
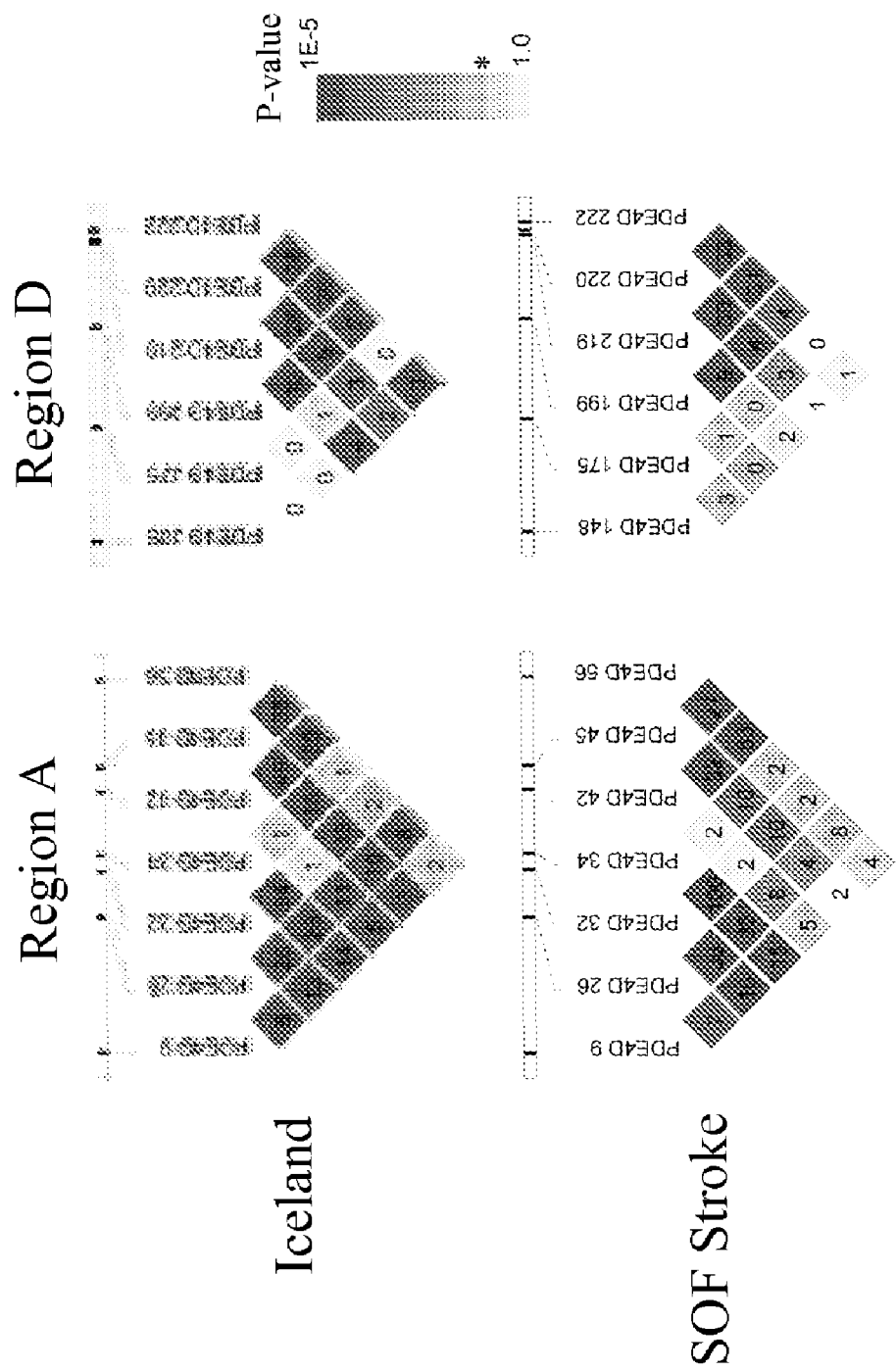
FIG. 2 illustrates a linkage disequilibrium plot comparison for the controls in the Study of Osteoporotic Fractures (SOF) stroke substudy and the Iceland study. The number in each square is the $r^2 \times 100$ value and the color intensity depicts the P value for each SNP pair. The color intensity legend is on a log scale and an asterisk marks the approximate location of 0.05. The diagrams above each plot depict the relative locations of the polymorphisms.

We investigated the linkage disequilibrium (LD) patterns in the SOF stroke population compared to the Icelandic stroke study population. FIG. 2 shows LD observed in controls of each population. Some SNP pairs exhibited LD differences between populations as measured by $r^2$. For example, the $r^2$ between SNP 42 and 45 was 0.49 in Iceland and 0.32 in SOF. Interestingly, both SNP 42 and 45 were significantly associated with stroke in Iceland but only SNP 42 in SOF. The LD in cases showed similar differences.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of predicting a predisposition for stroke in a female human without hypertension, the method comprising
    a) detecting in a sample from the female human the presence of an allele of a polymorphism in the PDE4D locus, wherein the presence of the allele is associated with a predisposition for stroke in female humans without hypertension, wherein the polymorphism is: SNP 9 A/G, wherein the presence of A is associated with a predisposition for stroke;
    b) predicting the presence of a predisposition for stroke in the person based on the presence of the allele in the sample, wherein the presence of the allele is associated with a predisposition for stroke in female humans without hypertension.

2. The method of claim 1, wherein the detecting step further comprises detecting an allele of SNP 219 C/T; and the predicting step comprises predicting a predisposition for stroke if the T allele of SNP 219 C/T is present.

3. The method of claim 1, wherein the detecting step further comprises detecting an allele of SNP 42 A/G; and
the predicting step comprises predicting a predisposition for stroke if the G allele of SNP 42 A/G is present.

4. The method of claim 1, wherein the detecting step further comprises detecting an allele of SNP 220 C/A; and
the predicting step comprises predicting a predisposition for stroke if the A allele of SNP 220 C/A is present.

5. The method of claim 1, wherein the detecting step further comprises detecting a microsatellite allele of AC008818-1; and
the predicting step comprises predicting a predisposition for stroke if 9 microsatellite repeats (TCAT) within AC008818-1 are present.

6. The method of claim 1, wherein the predicting step comprises recording the presence of a predisposition for stroke for the female human without hypertension.

7. The method of claim 1, wherein the polymorphism is detected with an oligonucleotide that distinguishes between at least two alternative alleles of the polymorphism.

8. The method of claim 7, wherein the oligonucleotide is detectably-labeled.

9. The method of claim 8, wherein the oligonucleotide is detectably-labeled with a fluorescent moiety.

10. The method of claim 9, wherein the fluorescent moiety is at the 5'-end of the oligonucleotide.

11. The method of claim 9, wherein the oligonucleotide further comprises a quencher moiety that quenches the fluorescent moiety when the oligonucleotide is intact.

12. The method of claim 1, wherein the detecting step further comprises detecting a polymorphism selected from the group consisting of:
SNP 219 C/T, wherein the presence of T is associated with a predisposition for stroke;
SNP 42 A/G, wherein the presence of G is associated with a predisposition for stroke;
SNP 220 C/A, wherein the presence of A is associated with a predisposition for stroke; and
microsatellite repeats (TCAT) within AC008818-1, wherein the presence of 9 microsatellite repeats (TCAT) is associated with a predisposition for stroke.

13. A computer implemented method for determining a predisposition for stroke in female humans without hypertension, the method comprising:
a) detecting in a sample from the female human without hypertension the presence of an allele of a polymorphism in the PDE4D locus, wherein the presence of the allele is associated with a predisposition for stroke in female humans without hypertension, wherein the polymorphisms is SNP 9 A/G;
b) receiving, at a host computer, information indicating the presence of the allele of a polymorphism of the PDE4D locus associated with a predisposition for stroke in female humans without hypertension; and
c) determining a predisposition for stroke in the female human without hypertension, wherein a predisposition for stroke is predicted if the female human without hypertension has:
an A in SNP9A/G.

14. The method of claim 13, further comprising a step of outputting the presence of a predisposition for stroke for the female human without hypertension.

15. The method of claim 13, wherein the detecting step further comprises detecting a polymorphism selected from the group consisting of SNP 219 C/T, SNP 42 A/G, SNP 220 C/A, microsatellite allele of AC008818-1 (TCAT9), and SNP 175 T/C; and
the determining step comprises determining a predisposition for stroke if the female human without hypertension has:
a T in SNP 219 C/T;
a G in SNP 42 A/G;
a A in SNP 220 C/A;
9 microsatellite repeats (TCAT) within AC008818-1; or
a T in SNP 175 T/C.

* * * * *

SEQUENCE LISTING

```
<160> NUMBER OF SEQ ID NOS: 113

<210> SEQ ID NO 1
<211> LENGTH: 486
<212> TYPE: DNA
<213> ORGANISM: Homo sapiens
<220> FEATURE:
<221> NAME/KEY: allele
<222> LOCATION: (242)...(242)
<223> OTHER INFORMATION: phosphodiesterase 4D (PDE4D) single nucleotide
      polymorphism SNP 9

<400> SEQUENCE: 1
aaattgatac agaatgatca acattgagag gtatccaagt aaacatactg gccctcaagg      60
ccaatgaaaa attttagaat ccaggcaaaa ataaaaaata agagtgaaaa attaagttgg     120
catgataaca aaatagacta tgtagtggaa tatcaaaagt aagagaaagg aatcctaaca     180
taaatgagag tacaacattt caacatatta ccataaaaag tttaaattgt ctaattcacc     240
trttgactca aatttacaaa aaagggaaat caaattattt gtaatatgtg agatgcatct     300
aaaacaacga aactcagaaa ggataataaa gataaaaatt aggcaaagac atgcaaagca     360
aatgcaaaaa aaaaaaagag cagctgtcat aactatggtt gcattcaaaa caaaaaacat     420
gaaataagac aaaaggggaa cttgataata ataaaggatg taactcacaa tgcagttcaa     480
tatgat                                                                486

<210> SEQ ID NO 2
<211> LENGTH: 628
<212> TYPE: DNA
<213> ORGANISM: Homo sapiens
<220> FEATURE:
<221> NAME/KEY: allele
<222> LOCATION: (285)...(285)
<223> OTHER INFORMATION: phosphodiesterase 4D (PDE4D) single nucleotide
      polymorphism SNP 26

<400> SEQUENCE: 2
cccgattaat tccctttcat cgtcctccat acccaaaggt cctgtcttgg accagggagg      60
ctcactgggc caagtattca tcacaaatgt taataaaatat aacctaattt taaaagaaat     120
atctccaaag agtgtagcct tctaggagac tgagtacaaa aaaaagaaag gggtggagca     180
ggacagagta tgaaagaaga ctgcaagaaa aggtcaggta caactgggag agaaaaatgc     240
agaagctgtg ggcatgcaag gccagaagtg tagccaagaa gcagraggtg aagtcaaagg     300
tggatgaagg gaaagaaaga tgaaatgaga gaaaaaatcc taggagtctt agcattggag     360
```

```
ggggaactca ggtgcgagaa atgatctaat aatagttgaa tggagagaaa atcaatgtat    420
ggtcaatctt cattatcaca gattatgtgt ttgcaaatcc acctacttgc taaaatttat    480
ctgtaatccc aaaagcaatc cttgcggcgc ttctgcagtc atttgtggac gagcgtgaag    540
cagtgaaaaa tttaagcagt gccacatgtg tatttccagc tgagggtgaa caagggatgc    600
tcagccatcg tgtttcagcc ctcatgct                                       628
```

<210> SEQ ID NO 3
<211> LENGTH: 634
<212> TYPE: DNA
<213> ORGANISM: Homo sapiens
<220> FEATURE:
<221> NAME/KEY: allele
<222> LOCATION: (290)...(290)
<223> OTHER INFORMATION: phosphodiesterase 4D (PDE4D) single nucleotide
      polymorphism SNP 32

<400> SEQUENCE: 3

```
aggaagggga acatcacact ctggggactg ttgtggggtg ggggaagcgg ggagggatag     60
tattaggaga tatacctaat gctaaatgat gagttaatgg gtgcagcaca ccagcatggc    120
acatgtatac atatgtaact aacctgcaca ttgtgcacat gtaccctaaa acttaaagtt    180
taataataat aaaattaaat taaaaaaaaa agaaaacct gtagctctgg tatcatagtg    240
gctgtagtga ctggttgaat gatttaatct atttcagcct cagttgccyy agctgttaga    300
ggagttaatt atatcagtcc tgccttataa tcatagcaat aattcccatt tccaaatgcc    360
tgccatgggt caggttcttg ctatgtcttt ggcacatatt atctttaagt ctcatcaact    420
ctgcaaggaa ggacaattg tcattcacag tttacagctg agaaagctga ggctcagatt    480
atttcagtaa gctgcctgaa gtcatgcagc taagtggcaa agccaggata taaacttcat    540
atgtatgttc acaaagtccc cgcttagtcc tccatggaat ttttagagtt atttaaaatg    600
acatgtgtga aagtgttttg aaaatagcaa agtt                                634
```

<210> SEQ ID NO 4
<211> LENGTH: 639
<212> TYPE: DNA
<213> ORGANISM: Homo sapiens
<220> FEATURE:
<221> NAME/KEY: allele
<222> LOCATION: (289)...(289)
<223> OTHER INFORMATION: phosphodiesterase 4D (PDE4D) single nucleotide
      polymorphism SNP 34

<400> SEQUENCE: 4

```
gctagatacc ataagagctg gataccagcc cagtgttgct gtttggattt gatcatactc     60
tcttgagtac aggaacaaga gggcagccta acattgtccc tgaagccctc tgcccacagc    120
cagtcagatc catgtccaac cttagcagct aggatgctgg ccatccctgt ggcccaggcc    180
ccatttgtac aagttctggg actggggtga aggtattctt gttataatgc cttttaaca    240 caattctggc cttttgggag agagagtcaa tgttttacac tctggggamt caacttgtgc    300
tcggattcac ctttggcaag ggtcctttag tggaatggac tctgcccagg gagtcagtgg    360
actgctgttt gctggttgat tttagacaag ttactttatg tttgtgggcc tcattttcct    420
ctgagcaaag acatctctaa cctgagtcac agcacaatct ttgtggtctg actctgtctg    480
gggcatggaa aattgtgtgt gtgtgtgtgt gtgtgtgtgt gtgtgtgcat gtgtgtgtct    540
ccagtcactg gttctgggga tgttcctcca aactgttctt gccttctttc tgttatccaa    600
acttttctgt gcagaagaac aagatttaag tttgaatgg                           639
```

<210> SEQ ID NO 5
<211> LENGTH: 711
<212> TYPE: DNA
<213> ORGANISM: Homo sapiens
<220> FEATURE:
<221> NAME/KEY: allele
<222> LOCATION: (289)...(289)
<223> OTHER INFORMATION: phosphodiesterase 4D (PDE4D) single nucleotide polymorphism SNP 42

<400> SEQUENCE: 5

```
ttatactgct ttacatgttt aaagcaaaga tatggtttta gcatcaaata ttaagaatgc      60
actccccaca tttttcttat taaatgtaat tgccagtttt tgtatatgtc attgtcctaa     120
tgctttcgag aaacttagac aaagagcaag accacagata aatggatcct tctgttcagg     180
tctcattacc tagaagagtt ttgactgcaa tatatgagta ctaaaagttg atggtttatg     240
ctaattttaa gtgtaatata ttttagaatt ttgtcacatg cattattart atgatttcat     300
attcatggcc ttaggaagat taatttaaac aataacaaca agaacaacaa caacaacaaa     360
atacaacaaa aaatttcccc catgtgccaa gagcaaattt tgaggtccat ttatccagat     420
aaagtgtttt gttatctgaa ccaagaacat gaactttatc tttatagtga ccacagactc     480
ccatctctag tatcatgatt tttaatttga attaaagcat ttttttttgc tttgttaaga     540
tgaggcaggc cttcttgctg acattttaaa aagcaactat ttttctttca gtttacacta     600
tgaggcattg gctccaactg tcagcattga aactgtcagc agttccctac caggaaactg     660
gttccaaggt ctagggtttc cttaggtaga ggctggcact gtgaaaataa t              711
```

<210> SEQ ID NO 6
<211> LENGTH: 631
<212> TYPE: DNA
<213> ORGANISM: Homo sapiens
<220> FEATURE:
<221> NAME/KEY: allele
<222> LOCATION: (288)...(288)
<223> OTHER INFORMATION: phosphodiesterase 4D (PDE4D) single nucleotide polymorphism SNP 45

<400> SEQUENCE: 6

```
tggcagggtt attccagctt tgtgccatga atcacagtca agctgcattt tgaaggaggc      60
tgtttgatgc atttgctagc tctgtttgtt ttatggggtc agtaaagtgg cagaggtcca     120
acaggagcag gttaaagcag gatgctggga tcaaagctta gagagcactt gagtcaggca     180
agttttaagt tttcccaccc ccaagcatct cagtccaaaa ctgagagcaa gcagcaaata     240
ttataataaa tgctttgggg acaggggtac acagcagata gggcacarta acaggagaaa     300
tgtaaaatga tggcagcaat acttttgttc actgtaatct gcagccaatt gaagacatac     360
actatgaata actaaaacat ttttatatga acaaaaatgc tcttcagtgg ttctgtttat     420
gtggtagagg gctgaatgaa aaaccatgcg cttgttgtaa aaaagcctta taaaaagtac     480
attaaacaca tacagacaca accataacag aagaaagtat gtggattgga atttgtgatt     540
ggagcagatc aaattaagcc agggaagccg ttattaggtt tgtatgattg ctgggggta      600
acttctgttg ctgacaaggt ttaggataaa g                                    631
```

<210> SEQ ID NO 7
<211> LENGTH: 648
<212> TYPE: DNA
<213> ORGANISM: Homo sapiens
<220> FEATURE:

```
<221> NAME/KEY: allele
<222> LOCATION: (357)...(357)
<223> OTHER INFORMATION: phosphodiesterase 4D (PDE4D) single nucleotide
      polymorphism SNP 56

<400> SEQUENCE: 7
tcagatggtt gtagatgtgt ggtgttattt ctgagcctct gttctgttcc attggtctat    60
atatctgttt tggtgccagt accgtgctat tttggttact gtagccttgt agtatagttt   120
gaagtcaggt agcgtgatgc ctccagtttg ttcttttgc ttaggattgt cttggctata    180
caggctcttt tttggttcca taaagatgct tttcctggct ttagttgttt cttctctagg   240
atattcttta catcgcaacc agaataagtc atcaaaggtc caattatgcc acattcttgc   300
tcaaagatct tcaatgaatc ttgatttcta tgtgataatg gttaatttcc tacatgwtta   360
acatgtactc tgaagctaga ctgcccggat tttgatcctg gtcccactac ttcctagttt   420
tgtaaccttg gaaaaattat tcaactcctt tgtgctttag ttgcctcggt gaaaaatggg   480
gataatcata gtgctgcctt atagggttgt tgtaataatt aaatgattat cctgcacata   540
gtaaacagtc aatgaattta tgctattatt attagtctgc tatttgtggg ctttcatatt   600
ttgtctcaaa tccaaccttc tctttactca ctatttctaa acacattg                648

<210> SEQ ID NO 8
<211> LENGTH: 498
<212> TYPE: DNA
<213> ORGANISM: Homo sapiens
<220> FEATURE:
<221> NAME/KEY: allele
<222> LOCATION: (230)...(230)
<223> OTHER INFORMATION: phosphodiesterase 4D (PDE4D) single nucleotide
      polymorphism SNP 222

<400> SEQUENCE: 8
gggccactgg cattaagaac aagcctgcca ataagataaa ctgtgaaaga agatcccgtt    60
cctagaacac aaagtgagag cacttgtgaa tccctgccca tgtactcaac tctttcgctg   120
tctttcttcc ctccatggaa gtcagactct cagctttgta ctcaaacctt ctggtgataa   180
tttgggacat cagccgtcct agaaaagtct ctctattgta ttggttttr ttaaacaaaa    240 taacctaata tgcttagtga atatgtctac acacatgtgc taaacatttg tttaattatt   300
taacttggaa aattttggtg tatcatttct aacagagata gtctttgtgc catcatataa   360
ctaacaaatt tgaaggcatt cattggcatc atgtatttc tctaatgagt cctaaattgt    420
tttctcatga caaataaaga gattccattt tagactagat tatttttgc ttatgttgcg    480 taaacttcag tcccatct                                                 498

<210> SEQ ID NO 9
<211> LENGTH: 495
<212> TYPE: DNA
<213> ORGANISM: Homo sapiens
<220> FEATURE:
<221> NAME/KEY: allele
<222> LOCATION: (228)...(228)
<223> OTHER INFORMATION: phosphodiesterase 4D (PDE4D) single nucleotide
      polymorphism SNP 220

<400> SEQUENCE: 9
aaacaacttt ctattcctag tggccctatt tttacattat ttttatctca cttccttaga    60
tttgaaattc atgacactta cttattcatt cacacataat gagaatgctt cttgagcaaa   120
tatggtgtat ttaaagctct gaatctgtgg agcagtgagg tctggcattt tagaccattg   180
```

-continued

```
taataaaata tggtgagcac aatccttgag gcatttatca tgtactgmag gaacagagag      240
aggagatgga gagttttcca cccaagggaa agatacagaa aataccgggc taagggaaca      300
acatttacta aatgtgaggc atggaaaatt atggctgaac taaggaatga caatctgctt      360
gatgtgaata gcgaaacctg gcaagagaga agaaaatttc aaatacagtc tatgggacct      420
gagagccaca gaggttttta gctgagtttt ggcatgatca tattcttgtt tttattgcat      480
cttgattact ctatt                                                        495
```

<210> SEQ ID NO 10
<211> LENGTH: 493
<212> TYPE: DNA
<213> ORGANISM: Homo sapiens
<220> FEATURE:
<221> NAME/KEY: allele
<222> LOCATION: (230)...(230)
<223> OTHER INFORMATION: phosphodiesterase 4D (PDE4D) single nucleotide
      polymorphism SNP 219

<400> SEQUENCE: 10

```
tccgggctaa ttctccaagc aaattttgtc cacagtcaac gacgggagtc cttcctgtat       60
cgatccgaca gcgattatga cctctctcca agtctatgt cccggaactc ctccattgcc      120
agtgatatgt aagtacaagg gcaggcaaag agagagaaaa ccgagtaaat ttatatctag      180
agctgatgac ataataaaac taatgacttt tgttcaactg tatcactcty ctccaatgta      240
gaaagaatat gaataaaatt atacaagcta gaaatgaatg gtagatttaa cctgagtgca      300
ctgtcactct tgattaacac acacacacac acacacacac acacacacac acgcatgtat      360
ttattttccc agaaaatact ttataggaaa actgagaatt aaattttta tggaaactaa      420 cacttaaatc attagcttat atttatgtag agcctgagtt ttagctacct aactacatgg      480
atattttcta ata                                                         493
```

<210> SEQ ID NO 11
<211> LENGTH: 496
<212> TYPE: DNA
<213> ORGANISM: Homo sapiens
<220> FEATURE:
<221> NAME/KEY: allele
<222> LOCATION: (231)...(231)
<223> OTHER INFORMATION: phosphodiesterase 4D (PDE4D) single nucleotide
      polymorphism SNP 199

<400> SEQUENCE: 11

```
cttttacatg ctgggtgatt ttggacaagg gggaaaagct acccataggg tttctgtgaa       60
tgttaagtga ataatacat ggaaagtgct tgaagtaatg gtagggacac agcaaaccaa      120
aaaaaatgct agccagttta ttattagaag ggaaaaactc ctattaatat tttcttgttt      180
atgtttgtgt tttcatgtta gtcttaaaac aagttactgt ttgagaatgt ragaatttta      240
accatttaca aaatggtgta tgatatgaca tgtatatgat ctctcacaag tgaaatgata      300
atggaaagtt tactgaaaat gtcttaacag ttctaggtaa aacttaattt ttccttaatt      360
tgaaaattaa taaagtatg aattagattt aatctaaatt tattattctg ttaaagtcac      420
atgaatgtgg aaaaaaatca gtatcacttc taactaaatc tggccttgaa acttctttga      480
catagtcttc ttaaaa                                                     496
```

<210> SEQ ID NO 12
<211> LENGTH: 492
<212> TYPE: DNA
<213> ORGANISM: Homo sapiens

```
<220> FEATURE:
<221> NAME/KEY: allele
<222> LOCATION: (231)...(231)
<223> OTHER INFORMATION: phosphodiesterase 4D (PDE4D) single nucleotide
      polymorphism SNP 175

<400> SEQUENCE: 12
aaaagagctt aaagaagaaa ttgcctctct ctcagaaaga attagtggga gaatctgatg      60
ttcttcatga aagaaaaaaa ttttagttga atcttgcata aaaagattag acagatggga     120
attgtcgagg gtggaggcac tgtacactac atgaagcata tttaaggaat gataacagtc    180
tagattgcta gcaagcttga ataggcaaaa taaaatagaa aggttaggga ytagttgaat     240
tagtcagaac tgttgagatt ccaagagaaa aacaaaattc acattttctg tgttgatcta     300
ttattgcaag gtgcattagt cagctattgc tacagtaatg ctaccgaaca atcaactaca    360
aaataccaat gacatttgct tcttgctcat agtcctacta atgggtcaga atagtgctgc    420
ttcaggctgc aggttgcctt catgcttgtt cttcatgttt ctccttcttg gaccagtgat    480
ctcccagggc gt                                                         492

<210> SEQ ID NO 13
<211> LENGTH: 506
<212> TYPE: DNA
<213> ORGANISM: Homo sapiens
<220> FEATURE:
<221> NAME/KEY: allele
<222> LOCATION: (228)...(228)
<223> OTHER INFORMATION: phosphodiesterase 4D (PDE4D) single nucleotide
      polymorphism SNP 148

<400> SEQUENCE: 13
tttctctatt cttgtctgac tgtcttattt tagaaagcca gttttcaagc tctgagattt      60
ctgagatttt ttcctccact taggctgttc tgttattagt acttgtaatt acattatgaa     120
attctaataa tgtttttcagt tctatcaggt tggtgacatt cttgtctata ctggctgttt    180
gtctgtcagt tcctgcattg ttttatcatg atttttagct tccttccrtt gggtttcaac    240
atactcctgt acttcaatga tcttcattcc aatccatatt ttgaattcta tttctgtcat    300
ttcagccatc tcagcctggt ttagaagctt gctttagaag ggacrcggtt gtttggagga    360
aaaaaggcac tctggccttt tgagttttca gggttcttgt gctgattctt tctcatcttt    420
gtggactttt ctacctttaa tgtttgaggt tgctgacatt tgaatgtttt ttttttcctt    480
ttatcctatt tgatgacctt gagggt                                         506

<210> SEQ ID NO 14
<211> LENGTH: 257
<212> TYPE: DNA
<213> ORGANISM: Homo sapiens
<220> FEATURE:
<221> NAME/KEY: repeat_region
<222> LOCATION: (108)...(139)
<223> OTHER INFORMATION: phosphodiesterase 4D (PDE4D) microsatellite
      AC008818-1
<223> OTHER INFORMATION: tandem repeat, (tcat)-8, allele -8

<400> SEQUENCE: 14
caactgagac ttagacgtgc tcactaagaa gcagcagaag aaagaacaga gtctgcttgg      60
tgaaggaata gccaccccag agaaggagta tggacttcta tacacaatca ttcattcatt    120
cattcattca ttcattcatt cactactcat gcatgatctt tgtccttatc ttcctccact    180
gtcacatgaa tacccaccca ctgcacctac ctgcttccta ttcctgagaa cccaggctca    240
```
cacacagagc catgttt                                                        257

<210> SEQ ID NO 15
<211> LENGTH: 261
<212> TYPE: DNA
<213> ORGANISM: Homo sapiens
<220> FEATURE:
<221> NAME/KEY: repeat_region
<222> LOCATION: (108)...(143)
<223> OTHER INFORMATION: phosphodiesterase 4D (PDE4D) microsatellite
      AC008818-1
<223> OTHER INFORMATION: tandem repeat, (tcat)-9, allele -4

<400> SEQUENCE: 15
caactgagac ttagacgtgc tcactaagaa gcagcagaag aaagaacaga gtctgcttgg    60
tgaaggaata gccaccccag agaaggagta tggacttcta tacacaatca ttcattcatt   120
cattcattca ttcattcatt cattcactac tcatgcatga tctttgtcct tatcttcctc   180
cactgtcaca tgaataccca cccactgcac ctacctgctt cctattcctg agaacccagg   240
ctcacacaca gagccatgtt t                                              261

<210> SEQ ID NO 16
<211> LENGTH: 265
<212> TYPE: DNA
<213> ORGANISM: Homo sapiens
<220> FEATURE:
<221> NAME/KEY: repeat_region
<222> LOCATION: (108)...(147)
<223> OTHER INFORMATION: phosphodiesterase 4D (PDE4D) microsatellite
      AC008818-1
<223> OTHER INFORMATION: tandem repeat, (tcat)-10, allele 0

<400> SEQUENCE: 16
caactgagac ttagacgtgc tcactaagaa gcagcagaag aaagaacaga gtctgcttgg    60
tgaaggaata gccaccccag agaaggagta tggacttcta tacacaatca ttcattcatt   120
cattcattca ttcattcatt cattcattca ctactcatgc atgatctttg tccttatctt   180
cctccactgt cacatgaata cccacccact gcacctacct gcttcctatt cctgagaacc   240
caggctcaca cacagagcca tgttt                                          265

<210> SEQ ID NO 17
<211> LENGTH: 269
<212> TYPE: DNA
<213> ORGANISM: Homo sapiens
<220> FEATURE:
<221> NAME/KEY: repeat_region
<222> LOCATION: (108)...(151)
<223> OTHER INFORMATION: phosphodiesterase 4D (PDE4D) microsatellite
      AC008818-1
<223> OTHER INFORMATION: tandem repeat, (tcat)-11, allele 4

<400> SEQUENCE: 17
caactgagac ttagacgtgc tcactaagaa gcagcagaag aaagaacaga gtctgcttgg    60
tgaaggaata gccaccccag agaaggagta tggacttcta tacacaatca ttcattcatt   120
cattcattca ttcattcatt cattcattca ttcactactc atgcatgatc tttgtcctta   180
tcttcctcca ctgtcacatg aatacccacc cactgcacct acctgcttcc tattcctgag   240
aacccaggct cacacacaga gccatgttt                                      269

<210> SEQ ID NO 18
<211> LENGTH: 273
<212> TYPE: DNA
<213> ORGANISM: Homo sapiens

```
<220> FEATURE:
<221> NAME/KEY: repeat_region
<222> LOCATION: (108)...(155)
<223> OTHER INFORMATION: phosphodiesterase 4D (PDE4D) microsatellite
      AC008818-1
<223> OTHER INFORMATION: tandem repeat, (tcat)-12, allele 8

<400> SEQUENCE: 18
caactgagac ttagacgtgc tcactaagaa gcagcagaag aaagaacaga gtctgcttgg      60
tgaaggaata gccaccccag agaaggagta tggacttcta tacacaatca ttcattcatt     120
cattcattca ttcattcatt cattcattca ttcattcact actcatgcat gatctttgtc     180
cttatcttcc tccactgtca catgaatacc cacccactgc acctacctgc ttcctattcc     240
tgagaaccca ggctcacaca cagagccatg ttt                                   273

<210> SEQ ID NO 19
<211> LENGTH: 277
<212> TYPE: DNA
<213> ORGANISM: Homo sapiens
<220> FEATURE:
<221> NAME/KEY: repeat_region
<222> LOCATION: (108)...(159)
<223> OTHER INFORMATION: phosphodiesterase 4D (PDE4D) microsatellite
      AC008818-1
<223> OTHER INFORMATION: tandem repeat, (tcat)-13, allele 12

<400> SEQUENCE: 19
caactgagac ttagacgtgc tcactaagaa gcagcagaag aaagaacaga gtctgcttgg      60
tgaaggaata gccaccccag agaaggagta tggacttcta tacacaatca ttcattcatt     120
cattcattca ttcattcatt cattcattca ttcattcatt cactactcat gcatgatctt     180
tgtccttatc ttcctccact gtcacatgaa tacccaccca ctgcacctac ctgcttccta     240
ttcctgagaa cccaggctca cacacagagc catgttt                               277

<210> SEQ ID NO 20
<211> LENGTH: 31
<212> TYPE: DNA
<213> ORGANISM: Artificial Sequence
<220> FEATURE:
<223> OTHER INFORMATION: linear array multiplex PCR 5'-biotinylated
      primer PDE4D120FB
<220> FEATURE:
<221> NAME/KEY: modified_base
<222> LOCATION: (1)...(1)
<223> OTHER INFORMATION: n = 5'-biotinylated a

<400> SEQUENCE: 20
natgagagta caacatttca acatattacc a                                     31

<210> SEQ ID NO 21
<211> LENGTH: 27
<212> TYPE: DNA
<213> ORGANISM: Artificial Sequence
<220> FEATURE:
<223> OTHER INFORMATION: linear array multiplex PCR 5'-biotinylated
      primer PDE4D121RB
<220> FEATURE:
<221> NAME/KEY: modified_base
<222> LOCATION: (1)...(1)
<223> OTHER INFORMATION: n = 5'-biotinylated g

<400> SEQUENCE: 21
nagtttcgtt gttttagatg catctca                                          27

<210> SEQ ID NO 22
```

```
<211> LENGTH: 20
<212> TYPE: DNA
<213> ORGANISM: Artificial Sequence
<220> FEATURE:
<223> OTHER INFORMATION: linear array multiplex PCR 5'-biotinylated
      primer PDE4D118FB
<220> FEATURE:
<221> NAME/KEY: modified_base
<222> LOCATION: (1)...(1)
<223> OTHER INFORMATION: n = 5'-biotinylated c

<400> SEQUENCE: 22
nagaagctgt gggcatgcaa                                              20

<210> SEQ ID NO 23
<211> LENGTH: 23
<212> TYPE: DNA
<213> ORGANISM: Artificial Sequence
<220> FEATURE:
<223> OTHER INFORMATION: linear array multiplex PCR 5'-biotinylated
      primer PDE4D119RB
<220> FEATURE:
<221> NAME/KEY: modified_base
<222> LOCATION: (1)...(1)
<223> OTHER INFORMATION: n = 5'-biotinylated g

<400> SEQUENCE: 23
nagttccccc tccaatgcta aga                                          23

<210> SEQ ID NO 24
<211> LENGTH: 26
<212> TYPE: DNA
<213> ORGANISM: Artificial Sequence
<220> FEATURE:
<223> OTHER INFORMATION: linear array multiplex PCR 5'-biotinylated
      primer PDE4D116FB
<220> FEATURE:
<221> NAME/KEY: modified_base
<222> LOCATION: (1)...(1)
<223> OTHER INFORMATION: n = 5'-biotinylated t

<400> SEQUENCE: 24
ncatagtggc tgtagtgact ggttga                                       26

<210> SEQ ID NO 25
<211> LENGTH: 20
<212> TYPE: DNA
<213> ORGANISM: Artificial Sequence
<220> FEATURE:
<223> OTHER INFORMATION: linear array multiplex PCR 5'-biotinylated
      primer PDE4D117RB
<220> FEATURE:
<221> NAME/KEY: modified_base
<222> LOCATION: (1)...(1)
<223> OTHER INFORMATION: n = 5'-biotinylated g

<400> SEQUENCE: 25
ncaggcattt ggaaatggga                                              20

<210> SEQ ID NO 26
<211> LENGTH: 21
<212> TYPE: DNA
<213> ORGANISM: Artificial Sequence
<220> FEATURE:
<223> OTHER INFORMATION: linear array multiplex PCR 5'-biotinylated
      primer PDE4D114RB
<220> FEATURE:
<221> NAME/KEY: modified_base
<222> LOCATION: (1)...(1)
<223> OTHER INFORMATION: n = 5'-biotinylated c
```

<400> SEQUENCE: 26
nacaattctg gccttttggg a                                        21

<210> SEQ ID NO 27
<211> LENGTH: 21
<212> TYPE: DNA
<213> ORGANISM: Artificial Sequence
<220> FEATURE:
<223> OTHER INFORMATION: linear array multiplex PCR 5'-biotinylated
      primer PDE4D115RB
<220> FEATURE:
<221> NAME/KEY: modified_base
<222> LOCATION: (1)...(1)
<223> OTHER INFORMATION: n = 5'-biotinylated a

<400> SEQUENCE: 27
naggaccctt gccaaaggtg a                                        21

<210> SEQ ID NO 28
<211> LENGTH: 29
<212> TYPE: DNA
<213> ORGANISM: Artificial Sequence
<220> FEATURE:
<223> OTHER INFORMATION: linear array multiplex PCR 5'-biotinylated
      primer PDE4D112FB
<220> FEATURE:
<221> NAME/KEY: modified_base
<222> LOCATION: (1)...(1)
<223> OTHER INFORMATION: n = 5'-biotinylated t

<400> SEQUENCE: 28
nctcattacc tagaagagtt ttgactgca                                29

<210> SEQ ID NO 29
<211> LENGTH: 30
<212> TYPE: DNA
<213> ORGANISM: Artificial Sequence
<220> FEATURE:
<223> OTHER INFORMATION: linear array multiplex PCR 5'-biotinylated
      primer PDE4D113RB
<220> FEATURE:
<221> NAME/KEY: modified_base
<222> LOCATION: (1)...(1)
<223> OTHER INFORMATION: n = 5'-biotinylated t

<400> SEQUENCE: 29
ntattgttta aattaatctt cctaaggcca                               30

<210> SEQ ID NO 30
<211> LENGTH: 20
<212> TYPE: DNA
<213> ORGANISM: Artificial Sequence
<220> FEATURE:
<223> OTHER INFORMATION: linear array multiplex PCR 5'-biotinylated
      primer PDE4D172FB
<220> FEATURE:
<221> NAME/KEY: modified_base
<222> LOCATION: (1)...(1)
<223> OTHER INFORMATION: n = 5'-biotinylated g

<400> SEQUENCE: 30
ngggacaggg gtacacagca                                          20

<210> SEQ ID NO 31
<211> LENGTH: 25
<212> TYPE: DNA
<213> ORGANISM: Artificial Sequence
<220> FEATURE:
<223> OTHER INFORMATION: linear array multiplex PCR 5'-biotinylated -continued

```
      primer PDE4D173RB
<220> FEATURE:
<221> NAME/KEY: modified_base
<222> LOCATION: (1)...(1)
<223> OTHER INFORMATION: n = 5'-biotinylated t

<400> SEQUENCE: 31
ncaattggct gcagattaca gtgaa                                          25

<210> SEQ ID NO 32
<211> LENGTH: 28
<212> TYPE: DNA
<213> ORGANISM: Artificial Sequence
<220> FEATURE:
<223> OTHER INFORMATION: linear array multiplex PCR 5'-biotinylated
      primer PDE4D174FB
<220> FEATURE:
<221> NAME/KEY: modified_base
<222> LOCATION: (1)...(1)
<223> OTHER INFORMATION: n = 5'-biotinylated t

<400> SEQUENCE: 32
ntgctcaaag atcttcaatg aatcttga                                       28

<210> SEQ ID NO 33
<211> LENGTH: 26
<212> TYPE: DNA
<213> ORGANISM: Artificial Sequence
<220> FEATURE:
<223> OTHER INFORMATION: linear array multiplex PCR 5'-biotinylated
      primer PDE4D175RB
<220> FEATURE:
<221> NAME/KEY: modified_base
<222> LOCATION: (1)...(1)
<223> OTHER INFORMATION: n = 5'-biotinylated t

<400> SEQUENCE: 33
ntaggaagta gtgggaccag gatcaa                                         26

<210> SEQ ID NO 34
<211> LENGTH: 26
<212> TYPE: DNA
<213> ORGANISM: Artificial Sequence
<220> FEATURE:
<223> OTHER INFORMATION: linear array multiplex PCR 5'-biotinylated
      primer PDE4D78FB
<220> FEATURE:
<221> NAME/KEY: modified_base
<222> LOCATION: (1)...(1)
<223> OTHER INFORMATION: n = 5'-biotinylated t

<400> SEQUENCE: 34
ngtctatact ggctgtttgt ctgtca                                         26

<210> SEQ ID NO 35
<211> LENGTH: 27
<212> TYPE: DNA
<213> ORGANISM: Artificial Sequence
<220> FEATURE:
<223> OTHER INFORMATION: linear array multiplex PCR 5'-biotinylated
      primer PDE4D79RB
<220> FEATURE:
<221> NAME/KEY: modified_base
<222> LOCATION: (1)...(1)
<223> OTHER INFORMATION: n = 5'-biotinylated g

<400> SEQUENCE: 35
nattggaatg aagatcattg aagtaca                                        27
```

<210> SEQ ID NO 36
<211> LENGTH: 33
<212> TYPE: DNA
<213> ORGANISM: Artificial Sequence
<220> FEATURE:
<223> OTHER INFORMATION: linear array multiplex PCR 5'-biotinylated primer PDE4D72FB
<220> FEATURE:
<221> NAME/KEY: modified_base
<222> LOCATION: (1)...(1)
<223> OTHER INFORMATION: n = 5'-biotinylated c

<400> SEQUENCE: 36
natgaagcat atttaaggaa tgataacagt cta                                    33

<210> SEQ ID NO 37
<211> LENGTH: 26
<212> TYPE: DNA
<213> ORGANISM: Artificial Sequence
<220> FEATURE:
<223> OTHER INFORMATION: linear array multiplex PCR 5'-biotinylated primer PDE4D73RB
<220> FEATURE:
<221> NAME/KEY: modified_base
<222> LOCATION: (1)...(1)
<223> OTHER INFORMATION: n = 5'-biotinylated t

<400> SEQUENCE: 37
ntctcttgga atctcaacag ttctga                                            26

<210> SEQ ID NO 38
<211> LENGTH: 31
<212> TYPE: DNA
<213> ORGANISM: Artificial Sequence
<220> FEATURE:
<223> OTHER INFORMATION: linear array multiplex PCR 5'-biotinylated primer PDE4D65FB
<220> FEATURE:
<221> NAME/KEY: modified_base
<222> LOCATION: (1)...(1)
<223> OTHER INFORMATION: n = 5'-biotinylated t

<400> SEQUENCE: 38
ntttcttgtt tatgtttgtg ttttcatgtt a                                      31

<210> SEQ ID NO 39
<211> LENGTH: 30
<212> TYPE: DNA
<213> ORGANISM: Artificial Sequence
<220> FEATURE:
<223> OTHER INFORMATION: linear array multiplex PCR 5'-biotinylated primer PDE4D66RB
<220> FEATURE:
<221> NAME/KEY: modified_base
<222> LOCATION: (1)...(1)
<223> OTHER INFORMATION: n = 5'-biotinylated a

<400> SEQUENCE: 39
ncatgtcata tcatacacca ttttgtaaat                                        30

<210> SEQ ID NO 40
<211> LENGTH: 25
<212> TYPE: DNA
<213> ORGANISM: Artificial Sequence
<220> FEATURE:
<223> OTHER INFORMATION: linear array multiplex PCR 5'-biotinylated primer PDE4D59FB
<220> FEATURE:
<221> NAME/KEY: modified_base
<222> LOCATION: (1)...(1)
<223> OTHER INFORMATION: n = 5'-biotinylated t

<400> SEQUENCE: 40
ngatatgtaa gtacaagggc aggca                                             25

<210> SEQ ID NO 41
<211> LENGTH: 27
<212> TYPE: DNA
<213> ORGANISM: Artificial Sequence
<220> FEATURE:
<223> OTHER INFORMATION: linear array multiplex PCR 5'-biotinylated
      primer PDE4D81RB
<220> FEATURE:
<221> NAME/KEY: modified_base
<222> LOCATION: (1)...(1)
<223> OTHER INFORMATION: n = 5'-biotinylated a

<400> SEQUENCE: 41
ngtgacagtg cactcaggtt aaatcta                                           27

<210> SEQ ID NO 42
<211> LENGTH: 21
<212> TYPE: DNA
<213> ORGANISM: Artificial Sequence
<220> FEATURE:
<223> OTHER INFORMATION: linear array multiplex PCR 5'-biotinylated
      primer PDE4D53FB
<220> FEATURE:
<221> NAME/KEY: modified_base
<222> LOCATION: (1)...(1)
<223> OTHER INFORMATION: n = 5'-biotinylated g

<400> SEQUENCE: 42
ntgagcacaa tccttgaggc a                                                 21

<210> SEQ ID NO 43
<211> LENGTH: 21
<212> TYPE: DNA
<213> ORGANISM: Artificial Sequence
<220> FEATURE:
<223> OTHER INFORMATION: linear array multiplex PCR 5'-biotinylated
      primer PDE4D54RB
<220> FEATURE:
<221> NAME/KEY: modified_base
<222> LOCATION: (1)...(1)
<223> OTHER INFORMATION: n = 5'-biotinylated c

<400> SEQUENCE: 43
nccttgggtg gaaaactctc c                                                 21

<210> SEQ ID NO 44
<211> LENGTH: 25
<212> TYPE: DNA
<213> ORGANISM: Artificial Sequence
<220> FEATURE:
<223> OTHER INFORMATION: linear array multiplex PCR 5'-biotinylated
      primer PDE4D47FB
<220> FEATURE:
<221> NAME/KEY: modified_base
<222> LOCATION: (1)...(1)
<223> OTHER INFORMATION: n = 5'-biotinylated c

<400> SEQUENCE: 44
nttctggtga taatttggga catca                                             25

<210> SEQ ID NO 45
<211> LENGTH: 28
<212> TYPE: DNA
<213> ORGANISM: Artificial Sequence
<220> FEATURE:

<223> OTHER INFORMATION: linear array multiplex PCR 5'-biotinylated
      primer PDE4D48RB
<220> FEATURE:
<221> NAME/KEY: modified_base
<222> LOCATION: (1)...(1)
<223> OTHER INFORMATION: n = 5'-biotinylated a

<400> SEQUENCE: 45
ncaaatgttt agcacatgtg tgtagaca                                         28

<210> SEQ ID NO 46
<211> LENGTH: 25
<212> TYPE: DNA
<213> ORGANISM: Artificial Sequence
<220> FEATURE:
<223> OTHER INFORMATION: linear array probe PDE4D182RQ
<220> FEATURE:
<221> NAME/KEY: modified_base
<222> LOCATION: (1)...(1)
<223> OTHER INFORMATION: n = a conjugated to bovine serum albumin (BSA)

<400> SEQUENCE: 46
ngagtacatg ttaatcatgt aggaa                                            25

<210> SEQ ID NO 47
<211> LENGTH: 25
<212> TYPE: DNA
<213> ORGANISM: Artificial Sequence
<220> FEATURE:
<223> OTHER INFORMATION: linear array probe PDE4D180FQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 47
ntcctacatg tttaacatgt actct                                            25

<210> SEQ ID NO 48
<211> LENGTH: 18
<212> TYPE: DNA
<213> ORGANISM: Artificial Sequence
<220> FEATURE:
<223> OTHER INFORMATION: linear array probe PDE4D178RQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 48
ntcctgttac tgtgccct                                                    18

<210> SEQ ID NO 49
<211> LENGTH: 18
<212> TYPE: DNA
<213> ORGANISM: Artificial Sequence
<220> FEATURE:
<223> OTHER INFORMATION: linear array probe PDE4D176FQ
<220> FEATURE:
<221> NAME/KEY: modified_base
<222> LOCATION: (1)...(1)
<223> OTHER INFORMATION: n = a conjugated to bovine serum albumin (BSA)

<400> SEQUENCE: 49
ngggcacaat aacaggag                                                    18

<210> SEQ ID NO 50
<211> LENGTH: 25
<212> TYPE: DNA

```
<213> ORGANISM: Artificial Sequence
<220> FEATURE:
<223> OTHER INFORMATION: linear array probe PDE4D92FQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 50
ncacatgcat tattaatatg atttc                                              25

<210> SEQ ID NO 51
<211> LENGTH: 25
<212> TYPE: DNA
<213> ORGANISM: Artificial Sequence
<220> FEATURE:
<223> OTHER INFORMATION: linear array probe PDE4D94RQ
<220> FEATURE:
<221> NAME/KEY: modified_base
<222> LOCATION: (1)...(1)
<223> OTHER INFORMATION: n = g conjugated to bovine serum albumin (BSA)

<400> SEQUENCE: 51
naaatcatac taataatgca tgtga                                              25

<210> SEQ ID NO 52
<211> LENGTH: 25
<212> TYPE: DNA
<213> ORGANISM: Artificial Sequence
<220> FEATURE:
<223> OTHER INFORMATION: linear array probe PDE4D184FQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 52
ncacatgcat tattaaaatg atttc                                              25

<210> SEQ ID NO 53
<211> LENGTH: 25
<212> TYPE: DNA
<213> ORGANISM: Artificial Sequence
<220> FEATURE:
<223> OTHER INFORMATION: linear array probe PDE4D185RQ
<220> FEATURE:
<221> NAME/KEY: modified_base
<222> LOCATION: (1)...(1)
<223> OTHER INFORMATION: n = g conjugated to bovine serum albumin (BSA)

<400> SEQUENCE: 53
naaatcattc taataatgca tgtga                                              25

<210> SEQ ID NO 54
<211> LENGTH: 20
<212> TYPE: DNA
<213> ORGANISM: Artificial Sequence
<220> FEATURE:
<223> OTHER INFORMATION: linear array probe PDE4D99RQ
<220> FEATURE:
<221> NAME/KEY: modified_base
<222> LOCATION: (1)...(1)
<223> OTHER INFORMATION: n = a conjugated to bovine serum albumin (BSA)

<400> SEQUENCE: 54
ncaagttgat tccccagagt                                                    20

<210> SEQ ID NO 55
<211> LENGTH: 18
```

```
<212> TYPE: DNA
<213> ORGANISM: Artificial Sequence
<220> FEATURE:
<223> OTHER INFORMATION: linear array probe PDE4D142FQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 55
nctggggact caacttgt                                                   18

<210> SEQ ID NO 56
<211> LENGTH: 21
<212> TYPE: DNA
<213> ORGANISM: Artificial Sequence
<220> FEATURE:
<223> OTHER INFORMATION: linear array probe PDE4D103RQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 56
ntctaacagc taaggcaact g                                               21

<210> SEQ ID NO 57
<211> LENGTH: 20
<212> TYPE: DNA
<213> ORGANISM: Artificial Sequence
<220> FEATURE:
<223> OTHER INFORMATION: linear array probe PDE4D101RQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 57
nctaacagct agggcaactg                                                 20

<210> SEQ ID NO 58
<211> LENGTH: 20
<212> TYPE: DNA
<213> ORGANISM: Artificial Sequence
<220> FEATURE:
<223> OTHER INFORMATION: linear array probe PDE4D102RQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 58
ntctaacagc tgaggcaact                                                 20

<210> SEQ ID NO 59
<211> LENGTH: 17
<212> TYPE: DNA
<213> ORGANISM: Artificial Sequence
<220> FEATURE:
<223> OTHER INFORMATION: linear array probe PDE4D100FQ
<220> FEATURE:
<221> NAME/KEY: modified_base
<222> LOCATION: (1)...(1)
<223> OTHER INFORMATION: n = a conjugated to bovine serum albumin (BSA)

<400> SEQUENCE: 59
ngttgcccca gctgtta                                                    17

<210> SEQ ID NO 60
```

```
<211> LENGTH: 20
<212> TYPE: DNA
<213> ORGANISM: Artificial Sequence
<220> FEATURE:
<223> OTHER INFORMATION: linear array probe PDE4D104FQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 60
naagaagcag aaggtgaagt                                               20

<210> SEQ ID NO 61
<211> LENGTH: 19
<212> TYPE: DNA
<213> ORGANISM: Artificial Sequence
<220> FEATURE:
<223> OTHER INFORMATION: linear array probe PDE4D106RQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 61
nttcacctcc tgcttcttg                                                19

<210> SEQ ID NO 62
<211> LENGTH: 24
<212> TYPE: DNA
<213> ORGANISM: Artificial Sequence
<220> FEATURE:
<223> OTHER INFORMATION: linear array probe PDE4D148FQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 62
nctaattcac ctattgactc aaat                                          24

<210> SEQ ID NO 63
<211> LENGTH: 23
<212> TYPE: DNA
<213> ORGANISM: Artificial Sequence
<220> FEATURE:
<223> OTHER INFORMATION: linear array probe PDE4D110RQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 63
nttgagtcaa caggtgaatt aga                                           23

<210> SEQ ID NO 64
<211> LENGTH: 29
<212> TYPE: DNA
<213> ORGANISM: Artificial Sequence
<220> FEATURE:
<223> OTHER INFORMATION: linear array probe PDE4D44FQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 64
ntctattgta ttggttttta ttaaacaaa                                     29
```

```
<210> SEQ ID NO 65
<211> LENGTH: 27
<212> TYPE: DNA
<213> ORGANISM: Artificial Sequence
<220> FEATURE:
<223> OTHER INFORMATION: linear array probe PDE4D46RQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 65
ntgtttaaca aaaccaata caataga                                              27

<210> SEQ ID NO 66
<211> LENGTH: 22
<212> TYPE: DNA
<213> ORGANISM: Artificial Sequence
<220> FEATURE:
<223> OTHER INFORMATION: linear array probe PDE4D158FQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 66
ntctcctcca atgtagaaag aa                                                  22

<210> SEQ ID NO 67
<211> LENGTH: 23
<212> TYPE: DNA
<213> ORGANISM: Artificial Sequence
<220> FEATURE:
<223> OTHER INFORMATION: linear array probe PDE4D154RQ
<220> FEATURE:
<221> NAME/KEY: modified_base
<222> LOCATION: (1)...(1)
<223> OTHER INFORMATION: n = a conjugated to bovine serum albumin (BSA)
<220> FEATURE:
<221> NAME/KEY: modified_base
<222> LOCATION: (2)...(2)
<223> OTHER INFORMATION: n = 5-propynyl dUTP
<220> FEATURE:
<221> NAME/KEY: modified_base
<222> LOCATION: (6)...(6)
<223> OTHER INFORMATION: n = 5-propynyl dUTP
<220> FEATURE:
<221> NAME/KEY: modified_base
<222> LOCATION: (13)...(13)
<223> OTHER INFORMATION: n = 5-propynyl dUTP

<400> SEQUENCE: 67
nntctntcta cantggagaa gag                                                 23

<210> SEQ ID NO 68
<211> LENGTH: 23
<212> TYPE: DNA
<213> ORGANISM: Artificial Sequence
<220> FEATURE:
<223> OTHER INFORMATION: linear array probe PDE4D151FQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 68
ntgtcctcca atgtagaaag aat                                                 23

<210> SEQ ID NO 69
<211> LENGTH: 23
<212> TYPE: DNA
```

```
<213> ORGANISM: Artificial Sequence
<220> FEATURE:
<223> OTHER INFORMATION: linear array probe PDE4D155RQ
<220> FEATURE:
<221> NAME/KEY: modified_base
<222> LOCATION: (1)...(1)
<223> OTHER INFORMATION: n = a conjugated to bovine serum albumin (BSA)
<220> FEATURE:
<221> NAME/KEY: modified_base
<222> LOCATION: (2)...(2)
<223> OTHER INFORMATION: n = 5-propynyl dUTP
<220> FEATURE:
<221> NAME/KEY: modified_base
<222> LOCATION: (6)...(6)
<223> OTHER INFORMATION: n = 5-propynyl dUTP
<220> FEATURE:
<221> NAME/KEY: modified_base
<222> LOCATION: (13)...(13)
<223> OTHER INFORMATION: n = 5-propynyl dUTP

<400> SEQUENCE: 69
nntctntcta cantggagaa cag                                           23

<210> SEQ ID NO 70
<211> LENGTH: 23
<212> TYPE: DNA
<213> ORGANISM: Artificial Sequence
<220> FEATURE:
<223> OTHER INFORMATION: linear array probe PDE4D50FQ
<220> FEATURE:
<221> NAME/KEY: modified_base
<222> LOCATION: (1)...(1)
<223> OTHER INFORMATION: n = a conjugated to bovine serum albumin (BSA)

<400> SEQUENCE: 70
ntcatgtact gcaggaacag aga                                           23

<210> SEQ ID NO 71
<211> LENGTH: 25
<212> TYPE: DNA
<213> ORGANISM: Artificial Sequence
<220> FEATURE:
<223> OTHER INFORMATION: linear array probe PDE4D89RQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 71
ntttctgttc cttcagtaca tgata                                         25

<210> SEQ ID NO 72
<211> LENGTH: 25
<212> TYPE: DNA
<213> ORGANISM: Artificial Sequence
<220> FEATURE:
<223> OTHER INFORMATION: linear array probe PDE4D61FQ
<220> FEATURE:
<221> NAME/KEY: modified_base
<222> LOCATION: (1)...(1)
<223> OTHER INFORMATION: n = g conjugated to bovine serum albumin (BSA)

<400> SEQUENCE: 72
ntttgagaat gtaagaattt taacc                                         25

<210> SEQ ID NO 73
<211> LENGTH: 26
<212> TYPE: DNA
<213> ORGANISM: Artificial Sequence
<220> FEATURE:
<223> OTHER INFORMATION: linear array probe PDE4D82RQ
```

```
<220> FEATURE:
<221> NAME/KEY: modified_base
<222> LOCATION: (1)...(1)
<223> OTHER INFORMATION: n = g conjugated to bovine serum albumin (BSA)

<400> SEQUENCE: 73
ngttaaaatt ctcacattct caaaca                                          26

<210> SEQ ID NO 74
<211> LENGTH: 24
<212> TYPE: DNA
<213> ORGANISM: Artificial Sequence
<220> FEATURE:
<223> OTHER INFORMATION: linear array probe PDE4D90FQ
<220> FEATURE:
<221> NAME/KEY: modified_base
<222> LOCATION: (1)...(1)
<223> OTHER INFORMATION: n = a conjugated to bovine serum albumin (BSA)

<400> SEQUENCE: 74
naaggttagg gactagttga atta                                            24

<210> SEQ ID NO 75
<211> LENGTH: 25
<212> TYPE: DNA
<213> ORGANISM: Artificial Sequence
<220> FEATURE:
<223> OTHER INFORMATION: linear array probe PDE4D70RQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 75
ntaattcaac taatccctaa cctttt                                          25

<210> SEQ ID NO 76
<211> LENGTH: 19
<212> TYPE: DNA
<213> ORGANISM: Artificial Sequence
<220> FEATURE:
<223> OTHER INFORMATION: linear array probe PDE4D75FQ
<220> FEATURE:
<221> NAME/KEY: modified_base
<222> LOCATION: (1)...(1)
<223> OTHER INFORMATION: n = c conjugated to bovine serum albumin (BSA)

<400> SEQUENCE: 76
nttccttcca ttgggtttc                                                  19

<210> SEQ ID NO 77
<211> LENGTH: 20
<212> TYPE: DNA
<213> ORGANISM: Artificial Sequence
<220> FEATURE:
<223> OTHER INFORMATION: linear array probe PDE4D83RQ
<220> FEATURE:
<221> NAME/KEY: modified_base
<222> LOCATION: (1)...(1)
<223> OTHER INFORMATION: n = t conjugated to bovine serum albumin (BSA)

<400> SEQUENCE: 77
ngaaacccaa cggaaggaag                                                 20

<210> SEQ ID NO 78
<211> LENGTH: 27
<212> TYPE: DNA
<213> ORGANISM: Artificial Sequence
<220> FEATURE:
```

<223> OTHER INFORMATION: kinetic thermal cycling (real-time PCR) primer
      PDE4D25RK

<400> SEQUENCE: 78
catgtgtgta gacatattca ctaagca                                           27

<210> SEQ ID NO 79
<211> LENGTH: 26
<212> TYPE: DNA
<213> ORGANISM: Artificial Sequence
<220> FEATURE:
<223> OTHER INFORMATION: kinetic thermal cycling (real-time PCR) primer
      PDE4D26FKA

<400> SEQUENCE: 79
aagtctctct attgtattgg ttttta                                            26

<210> SEQ ID NO 80
<211> LENGTH: 24
<212> TYPE: DNA
<213> ORGANISM: Artificial Sequence
<220> FEATURE:
<223> OTHER INFORMATION: kinetic thermal cycling (real-time PCR) primer
      PDE4D27FKG

<400> SEQUENCE: 80
gtctctctat tgtattggtt tttg                                              24

<210> SEQ ID NO 81
<211> LENGTH: 20
<212> TYPE: DNA
<213> ORGANISM: Artificial Sequence
<220> FEATURE:
<223> OTHER INFORMATION: kinetic thermal cycling (real-time PCR) primer
      PDE4D28RK

<400> SEQUENCE: 81
gggtggaaaa ctctccatct                                                   20

<210> SEQ ID NO 82
<211> LENGTH: 22
<212> TYPE: DNA
<213> ORGANISM: Artificial Sequence
<220> FEATURE:
<223> OTHER INFORMATION: kinetic thermal cycling (real-time PCR) primer
      PDE4D29FK

<400> SEQUENCE: 82
tgaggcattt atcatgtact ga                                                22

<210> SEQ ID NO 83
<211> LENGTH: 21
<212> TYPE: DNA
<213> ORGANISM: Artificial Sequence
<220> FEATURE:
<223> OTHER INFORMATION: kinetic thermal cycling (real-time PCR) primer
      PDE4D30FKC

<400> SEQUENCE: 83
gaggcattta tcatgtactg c                                                 21

<210> SEQ ID NO 84
<211> LENGTH: 26
<212> TYPE: DNA
<213> ORGANISM: Artificial Sequence
<220> FEATURE:
<223> OTHER INFORMATION: kinetic thermal cycling (real-time PCR) primer -continued

PDE4D31FK

<400> SEQUENCE: 84 atgactttg ttcaactgta tcactc                                26

<210> SEQ ID NO 85
<211> LENGTH: 23
<212> TYPE: DNA
<213> ORGANISM: Artificial Sequence
<220> FEATURE:
<223> OTHER INFORMATION: kinetic thermal cycling (real-time PCR) primer
    PDE4D32RKC

<400> SEQUENCE: 85
tcatattctt tctacattgg agg                                  23

<210> SEQ ID NO 86
<211> LENGTH: 24
<212> TYPE: DNA
<213> ORGANISM: Artificial Sequence
<220> FEATURE:
<223> OTHER INFORMATION: kinetic thermal cycling (real-time PCR) primer
    PDE4D33RKT

<400> SEQUENCE: 86
ttcatattct ttctacattg gaga                                 24

<210> SEQ ID NO 87
<211> LENGTH: 26
<212> TYPE: DNA
<213> ORGANISM: Artificial Sequence
<220> FEATURE:
<223> OTHER INFORMATION: kinetic thermal cycling (real-time PCR) primer
    PDE4D34RK

<400> SEQUENCE: 87
acatgtcata tcatacacca ttttgt                               26

<210> SEQ ID NO 88
<211> LENGTH: 25
<212> TYPE: DNA
<213> ORGANISM: Artificial Sequence
<220> FEATURE:
<223> OTHER INFORMATION: kinetic thermal cycling (real-time PCR) primer
    PDE4D35RKA

<400> SEQUENCE: 88
aaacaagtta ctgtttgaga atgta                                25

<210> SEQ ID NO 89
<211> LENGTH: 24
<212> TYPE: DNA
<213> ORGANISM: Artificial Sequence
<220> FEATURE:
<223> OTHER INFORMATION: kinetic thermal cycling (real-time PCR) primer
    PDE4D36RKG

<400> SEQUENCE: 89
aacaagttac tgtttgagaa tgtg                                 24

<210> SEQ ID NO 90
<211> LENGTH: 24
<212> TYPE: DNA
<213> ORGANISM: Artificial Sequence
<220> FEATURE:
<223> OTHER INFORMATION: kinetic thermal cycling (real-time PCR) primer
    PDE4D37RK -continued

```
<400> SEQUENCE: 90
ttggaatctc aacagttctg acta                                          24

<210> SEQ ID NO 91
<211> LENGTH: 25
<212> TYPE: DNA
<213> ORGANISM: Artificial Sequence
<220> FEATURE:
<223> OTHER INFORMATION: kinetic thermal cycling (real-time PCR) primer
      PDE4D38RKC

<400> SEQUENCE: 91
aaaataaaat agaaaggtta gggac                                         25

<210> SEQ ID NO 92
<211> LENGTH: 25
<212> TYPE: DNA
<213> ORGANISM: Artificial Sequence
<220> FEATURE:
<223> OTHER INFORMATION: kinetic thermal cycling (real-time PCR) primer
      PDE4D39FKT

<400> SEQUENCE: 92
aaaataaaat agaaaggtta gggat                                         25

<210> SEQ ID NO 93
<211> LENGTH: 23
<212> TYPE: DNA
<213> ORGANISM: Artificial Sequence
<220> FEATURE:
<223> OTHER INFORMATION: kinetic thermal cycling (real-time PCR) primer
      PDE4D40RK

<400> SEQUENCE: 93
gattggaatg aagatcattg aag                                           23

<210> SEQ ID NO 94
<211> LENGTH: 21
<212> TYPE: DNA
<213> ORGANISM: Artificial Sequence
<220> FEATURE:
<223> OTHER INFORMATION: kinetic thermal cycling (real-time PCR) primer
      PDE4D41FKA

<400> SEQUENCE: 94
atgattttta gcttccttcc a                                             21

<210> SEQ ID NO 95
<211> LENGTH: 19
<212> TYPE: DNA
<213> ORGANISM: Artificial Sequence
<220> FEATURE:
<223> OTHER INFORMATION: kinetic thermal cycling (real-time PCR) primer
      PDE4D42FKG

<400> SEQUENCE: 95
gatttttagc ttccttccg                                                19

<210> SEQ ID NO 96
<211> LENGTH: 25
<212> TYPE: DNA
<213> ORGANISM: Artificial Sequence
<220> FEATURE:
<223> OTHER INFORMATION: kinetic thermal cycling (real-time PCR) primer
      PDE4D122FK
```

-continued

<400> SEQUENCE: 96
attttagaat tttgtcacat gcatt                                    25

<210> SEQ ID NO 97
<211> LENGTH: 22
<212> TYPE: DNA
<213> ORGANISM: Artificial Sequence
<220> FEATURE:
<223> OTHER INFORMATION: kinetic thermal cycling (real-time PCR) primer
      PDE4D123RKA

<400> SEQUENCE: 97
ggccatgaat atgaaatcat at                                       22

<210> SEQ ID NO 98
<211> LENGTH: 22
<212> TYPE: DNA
<213> ORGANISM: Artificial Sequence
<220> FEATURE:
<223> OTHER INFORMATION: kinetic thermal cycling (real-time PCR) primer
      PDE4D124RKG

<400> SEQUENCE: 98
ggccatgaat atgaaatcat ac                                       22

<210> SEQ ID NO 99
<211> LENGTH: 21
<212> TYPE: DNA
<213> ORGANISM: Artificial Sequence
<220> FEATURE:
<223> OTHER INFORMATION: kinetic thermal cycling (real-time PCR) primer
      PDE4D125RK

<400> SEQUENCE: 99
aggtgaatcc gagcacaagt t                                        21

<210> SEQ ID NO 100
<211> LENGTH: 20
<212> TYPE: DNA
<213> ORGANISM: Artificial Sequence
<220> FEATURE:
<223> OTHER INFORMATION: kinetic thermal cycling (real-time PCR) primer
      PDE4D126FKA

<400> SEQUENCE: 100
atgttttaca ctctggggaa                                          20

<210> SEQ ID NO 101
<211> LENGTH: 21
<212> TYPE: DNA
<213> ORGANISM: Artificial Sequence
<220> FEATURE:
<223> OTHER INFORMATION: kinetic thermal cycling (real-time PCR) primer
      PDE4D127FKC

<400> SEQUENCE: 101
aatgttttac actctgggga c                                        21

<210> SEQ ID NO 102
<211> LENGTH: 24
<212> TYPE: DNA
<213> ORGANISM: Artificial Sequence
<220> FEATURE:
<223> OTHER INFORMATION: kinetic thermal cycling (real-time PCR) primer
      PDE4D131FK

<400> SEQUENCE: 102
ttaatctatt tcagcctcag ttgc                                           24

<210> SEQ ID NO 103
<211> LENGTH: 26
<212> TYPE: DNA
<213> ORGANISM: Artificial Sequence
<220> FEATURE:
<223> OTHER INFORMATION: kinetic thermal cycling (real-time PCR) primer
      PDE4D132RKC

<400> SEQUENCE: 103
gatataatta actcctctaa cagctg                                         26

<210> SEQ ID NO 104
<211> LENGTH: 27
<212> TYPE: DNA
<213> ORGANISM: Artificial Sequence
<220> FEATURE:
<223> OTHER INFORMATION: kinetic thermal cycling (real-time PCR) primer
      PDE4D133RKT

<400> SEQUENCE: 104
tgatataatt aactcctcta acagcta                                        27

<210> SEQ ID NO 105
<211> LENGTH: 22
<212> TYPE: DNA
<213> ORGANISM: Artificial Sequence
<220> FEATURE:
<223> OTHER INFORMATION: kinetic thermal cycling (real-time PCR) primer
      PDE4D134RK

<400> SEQUENCE: 105 tctttcccctt catccaccttt tg                                           22

<210> SEQ ID NO 106
<211> LENGTH: 20
<212> TYPE: DNA
<213> ORGANISM: Artificial Sequence
<220> FEATURE:
<223> OTHER INFORMATION: kinetic thermal cycling (real-time PCR) primer
      PDE4D135FKA

<400> SEQUENCE: 106
aagtgtagcc aagaagcaga                                                20

<210> SEQ ID NO 107
<211> LENGTH: 18
<212> TYPE: DNA
<213> ORGANISM: Artificial Sequence
<220> FEATURE:
<223> OTHER INFORMATION: kinetic thermal cycling (real-time PCR) primer
      PDE4D136FKG

<400> SEQUENCE: 107
gtgtagccaa gaagcagg                                                  18

<210> SEQ ID NO 108
<211> LENGTH: 25
<212> TYPE: DNA
<213> ORGANISM: Artificial Sequence
<220> FEATURE:
<223> OTHER INFORMATION: kinetic thermal cycling (real-time PCR) primer
      PDE4D166RK

<400> SEQUENCE: 108

```
gaacaaaagt attgctgcca tcatt                                           25

<210> SEQ ID NO 109
<211> LENGTH: 18
<212> TYPE: DNA
<213> ORGANISM: Artificial Sequence
<220> FEATURE:
<223> OTHER INFORMATION: kinetic thermal cycling (real-time PCR) primer
      PDE4D167FKA

<400> SEQUENCE: 109
acagcagata gggcacaa                                                   18

<210> SEQ ID NO 110
<211> LENGTH: 18
<212> TYPE: DNA
<213> ORGANISM: Artificial Sequence
<220> FEATURE:
<223> OTHER INFORMATION: kinetic thermal cycling (real-time PCR) primer
      PDE4D168FKG

<400> SEQUENCE: 110
acagcagata gggcacag                                                   18

<210> SEQ ID NO 111
<211> LENGTH: 26
<212> TYPE: DNA
<213> ORGANISM: Artificial Sequence
<220> FEATURE:
<223> OTHER INFORMATION: kinetic thermal cycling (real-time PCR) primer
      PDE4D169FK

<400> SEQUENCE: 111
tcaatgaatc ttgatttcta tgtgat                                          26

<210> SEQ ID NO 112
<211> LENGTH: 25
<212> TYPE: DNA
<213> ORGANISM: Artificial Sequence
<220> FEATURE:
<223> OTHER INFORMATION: kinetic thermal cycling (real-time PCR) primer
      PDE4D170FKT

<400> SEQUENCE: 112
gtctagcttc agagtacatg ttaaa                                           25

<210> SEQ ID NO 113
<211> LENGTH: 26
<212> TYPE: DNA
<213> ORGANISM: Artificial Sequence
<220> FEATURE:
<223> OTHER INFORMATION: kinetic thermal cycling (real-time PCR) primer
      PDE4D171FKA

<400> SEQUENCE: 113
agtctagctt cagagtacat gttaat                                          26
```